US012776395B2

(12) United States Patent
D'Agostino et al.

(10) Patent No.: US 12,776,395 B2
(45) Date of Patent: Oct. 27, 2026

(54) GENERATION AND TRANSMISSION OF OPERATIVE NOTES

(71) Applicant: DOC BUDDY INC., Greenwood Village, CO (US)

(72) Inventors: Philip A. D'Agostino, Greenwood Village, CO (US); Jason A. Dell, Highlands Ranch, CO (US); Ashley A. Bye, St. Louis Park, MN (US)

(73) Assignee: DOC BUDDY INC., Greenwood Village, CO (US)

( * ) Notice: Subject to any disclaimer, the term of this patent is extended or adjusted under 35 U.S.C. 154(b) by 228 days.

(21) Appl. No.: 17/935,742

(22) Filed: Sep. 27, 2022

(65) Prior Publication Data

US 2023/0113548 A1 Apr. 13, 2023

Related U.S. Application Data

(60) Provisional application No. 63/250,841, filed on Sep. 30, 2021.

(51) Int. Cl.

*G16H 10/60* (2018.01)
*G10L 15/26* (2006.01)
*G16H 30/40* (2018.01)

(52) U.S. Cl.

CPC ............. *G16H 10/60* (2018.01); *G10L 15/26* (2013.01); *G16H 30/40* (2018.01)

(58) Field of Classification Search

CPC ........ G16H 10/60; G16H 30/40; G10L 15/26; G10L 2015/223; G10L 15/22

See application file for complete search history.

(56) References Cited

U.S. PATENT DOCUMENTS

| | | | | |
|---|---|---|---|---|
| 11,610,654 B1 * | 3/2023 | White | ..................... | G16H 70/60 |
| 2002/0194029 A1 * | 12/2002 | Guan | ..................... | G06Q 10/10 705/3 |
| 2004/0193449 A1 * | 9/2004 | Wildman | ............... | G16H 40/67 705/2 |
| 2005/0154613 A1 * | 7/2005 | Kade | ..................... | G16H 15/00 705/2 |

(Continued)

OTHER PUBLICATIONS

Biswas et al (Interoperability and Synchronization Management of Blockchain-Based Decentralized e-Health Systems) (Year: 2020).*

*Primary Examiner* — Mamon Obeid

(74) *Attorney, Agent, or Firm* — Dorsey & Whitney LLP

(57) ABSTRACT

An example method for generating an operative note includes receiving, from a provider device, a request for generation of an operative note corresponding to a medical procedure, where the operative note is associated with an appointment for the medical procedure to be performed and a patient identifier of an electronic medical record. A dictation interface is presented to the provider device and the operative note is generated by displaying, in the dictation interface, text generated based on audio input received at the provider device through the dictation interface. The operative note is finalized responsive to receipt of a provider approval indicating accuracy of the operative note, where the provider approval is authorized based on the electronic medical record. The finalized operative note is transmitted to the electronic medical record associated with the patient identifier.

20 Claims, 12 Drawing Sheets

(56) References Cited

U.S. PATENT DOCUMENTS

| | | | | |
|---|---|---|---|---|
| 2008/0288291 | A1* | 11/2008 | Bartelt | G16H 40/63 705/3 |
| 2009/0125332 | A1* | 5/2009 | Martin | G16H 10/60 705/2 |
| 2010/0036676 | A1* | 2/2010 | Safdi | G16H 15/00 705/2 |
| 2012/0173281 | A1* | 7/2012 | DiLella | G16H 10/20 705/3 |
| 2012/0304054 | A1* | 11/2012 | Orf | G16H 40/20 715/255 |
| 2016/0070860 | A1* | 3/2016 | Saliba | G16H 10/60 705/3 |
| 2016/0098523 | A1* | 4/2016 | Laskin | G16H 10/60 705/3 |
| 2016/0103810 | A1* | 4/2016 | Hanning | G16H 30/40 715/226 |
| 2020/0227149 | A1* | 7/2020 | Hussam | G16H 10/60 |
| 2020/0278999 | A1* | 9/2020 | Mukherji | G06F 16/9038 |
| 2021/0304881 | A1* | 9/2021 | White | G06K 7/1413 |
| 2022/0148689 | A1* | 5/2022 | Gill | G16H 10/60 |
| 2025/0022462 | A1* | 1/2025 | D'Agostino | G06F 3/04886 |
| 2025/0329441 | A1* | 10/2025 | Stimart | G16H 40/20 |

* cited by examiner

1100

DATE OF SURGERY : [ ]

PATIENT ID: [ ]

PREOPERATIVE DIAGNOSIS:

[ ]

POSTOPERATIVE DIAGNOSIS:

[Same]

PROCEDURE:

[ ]

SURGEON: [ ]

ASSISTANT: [ ]

ANESTHESIA: [ ]

EBL: [ ]

SPECIMEN: [ ]

DRAIN: [ ]

COMPLICATIONS: [None]

IMPLANTS if applicable: [ ]

INDICATIONS:

[ ]

DETAILS OF PROCEDURE:

[ ]

FIG. 12

1200

CARPAL TUNNEL RELEASE

DATE OF SURGERY : [ ]

PATIENT ID: [ ]

PREOPERATIVE DIAGNOSIS:

[ ] Carpal tunnel syndrome

POSTOPERATIVE DIAGNOSIS:

[Same]

PROCEDURE:

[ ] Carpal tunnel release

SURGEON: [ ]

ASSISTANT: [ ]

ANESTHESIA: [ ] Local and IV anesthesia

SPECIMEN: None

DRAIN: None

COMPLICATIONS: [None]

IMPLANTS if applicable: None

INDICATIONS:

[The patient presented with continued symptoms of carpal tunnel syndrome despite conservative treatment. Further options were discussed and the patient elected to move forward with surgery. Informed consent was obtained.]

DETAILS OF PROCEDURE:

[The patient was seen and identified in the preoperative holding area. The correct site was marked. The patient was brought back to the operating room and placed supine on the operating room table. A timeout was performed. After the patient received IV anesthesia by the anesthesiologist I infiltrated 6 mL of 0.5% bupivacaine with epinephrine in the proximal palm in line with the ring finger for local block under aseptic technique.

The upper extremity was then prepped and draped in the usual sterile fashion. The limb was exsanguinated with an Esmarch and the forearm tourniquet inflated to 250 mmHg. I made an incision in line with the ring finger in the proximal palm. Sharp dissection was carried down through the longitudinal fibers of the palmar fascia. Blunt retractors were placed deeper. I transected through the transverse carpal ligament fibers mid to distal aspect staying just radial to the hook of the hamate. The most distal portion was released with a tenotomy scissor confirming visualization of the fat pad and release of any tight fascial bands.]

FIG. 13

1300

LEFT ACHILLES TENDON REPAIR

DATE OF SURGERY : [ ]

PATIENT ID: [ ]

PREOPERATIVE DIAGNOSIS:

[Traumatic left Achilles tendon rupture]

POSTOPERATIVE DIAGNOSIS:

[Same]

PROCEDURE:

[Open repair left traumatic Achilles tendon rupture]

ANESTHESIA: [General with regional block for postoperative pain control]

Estimated blood loss: [minimal]

Tourniquet time: [Approximately 60 minutes]

IV fluids: [Approximately 500 LR]

Complications: [None]

INDICATIONS:

[The patient was seen and examined by me in the office. Please refer to my office notes for detailed information. I visited with the patient today and went over the surgical consent and surgical procedure in detail. Operative risks and benefits were discussed including the risks of anesthesia, infection, injury of normal structures, failure to relieve symptoms, worsening of symptoms, need for further surgery, and additional risks. All questions were answered. The patient agreed to proceed with the scheduled procedure.]

OPERATIVE NOTE:

The patient is a []-year-old [male/female] who unfortunately suffered a traumatic injury to [his/her] left Achilles while performing sporting activities approximately [] ago. [He/She] was subsequently seen in our orthopedic clinic where a traumatic Achilles tendon rupture was diagnosed with a notable palpable defect within the mid substance of the Achilles as well as a positive Thompson test. With this appreciated, both conservative as well as surgical treatment options were discussed with [him/her] and after the risks and benefits were thoroughly elucidated the patient agreed and wished to proceed with surgical intervention.

FIG. 14

GENERATION AND TRANSMISSION OF OPERATIVE NOTES

CROSS REFERENCE TO RELATED APPLICATION

This application is related to and claims the benefit of priority of U.S. Provisional Application No. 63/250,841 filed 30 Sep. 2020 and titled "GENERATION AND TRANSMISSION OF OPERATIVE NOTES," which is hereby incorporated by reference in its entirety for all purposes.

BACKGROUND

Operative notes detail surgical and other procedures and typically form an important part of patient medical records. Operative notes are often dictated by medical providers after an event (e.g., a surgery or a procedure) and a printed operative note is delivered to the provider sometime (e.g., days or weeks) after the initial dictation for review and signature. Delays between dictation and approval of a finalized operative note may generate errors or inconsistencies as providers may have difficulty recalling the specific event. Activities such as billing for the event and viewing the medical record (e.g., by other providers and surgery staff), may be delayed by the delay in generating and finalizing of operative notes.

Additionally, adding images or other information from the event to an operative note may involve or require transmitting the data using multiple devices, including unsecured devices. Using unsecured devices to transmit data from the event may adversely affect patient and/or network privacy and security. For example, the network of the unsecured device is vulnerable to cyberattacks and sensitive medical data may be transmitted to an external source without patient authorization. Additionally, adding images or other information from the event to the operative note may take days or weeks which may cause delays for other activities such as billing for the event and may also generate errors or inconsistencies as providers may have difficulty recalling the specific event. Immediate post op notes (IPON) may be used by some providers and/or organizations to provide information about procedures. IPONs are often hand written by providers and, accordingly, may be difficult to interpret and do not include image information from or related to the event. Additionally, providers often create both an IPON and formal operative note, duplicating efforts and adding more administrative tasks for providers.

SUMMARY

Methods of generating operative notes are described herein. An example method includes receiving, from a provider device, a request for generation of an operative note corresponding to a medical procedure, where the operative note is associated with an appointment for the medical procedure to be performed and a patient identifier of an electronic medical record. A dictation interface is presented to the provider device and the operative note is generated by displaying, in the dictation interface, text generated based on audio input received at the provider device through the dictation interface. The operative note is finalized responsive to receipt of a provider approval indicating accuracy of the operative note, where the provider approval is authorized based on the electronic medical record. The finalized operative note is transmitted to the electronic medical record associated with the patient identifier.

Systems for generating operative notes are described herein. An example system includes one or more processors and memory encoding instructions which, when executed by the one or more processors, cause the system to perform operations including presenting, responsive to a request to generate an operative note corresponding to a medical procedure, wherein the operative note is associated with an appointment for the medical procedure to be performed and a patient identifier of an electronic medical record, a dictation interface at a provider device in communication with the system, where one or more elements of the dictation interface are rendered based on information obtained by the system from the electronic medical record using the patient identifier. The operations further include generating the operative note by displaying, in the dictation interface, text generated based on audio input received at the provider device through the dictation interface and transmitting the generated operative note to the electronic medical record associated with the patient identifier and to a practice management system of a facility associated with the appointment.

Non-transitory computer readable media encoded with instructions for generating operative notes are described herein. Example non-transitory computer readable media are encoded with instructions that, when executed by one or more processors of an operative note system to perform operations including receiving, from a provider device, a request for generation of an operative note, where the operative note is associated with a patient identifier and an appointment for the medical procedure to be performed. The operations further include presenting a dictation interface to the provider device and generating the operative note by displaying, in the dictation interface, text generated based on audio input received at the provider device through the dictation interface. The operations further include finalizing the operative note responsive to receipt of a provider approval indicating accuracy of the operative note and transmitting the finalized operative note to an electronic medical record associated with the patient identifier.

Additional embodiments and features are set forth in part in the description that follows, and will become apparent to those skilled in the art upon examination of the specification and may be learned by the practice of the disclosed subject matter. A further understanding of the nature and advantages of the present disclosure may be realized by reference to the remaining portions of the specification and the drawings, which form a part of this disclosure. One of skill in the art will understand that each of the various aspects and features of the disclosure may advantageously be used separately in some instances, or in combination with other aspects and features of the disclosure in other instances.

BRIEF DESCRIPTION OF THE DRAWINGS

The description will be more fully understood with reference to the following figures in which components are not drawn to scale, which are presented as various examples of the present disclosure and should not be construed as a complete recitation of the scope of the disclosure, characterized in that:

FIG. 12 illustrates an example template for generation of an operative node, in accordance with various embodiments of the disclosure.

FIG. 13 illustrates an example procedure specific template for generation of an operative note, in accordance with various embodiments of the disclosure.

FIG. 14 illustrates an example procedure specific template for generation of an operative note, in accordance with various embodiments of the disclosure.

DETAILED DESCRIPTION

Figure 1:
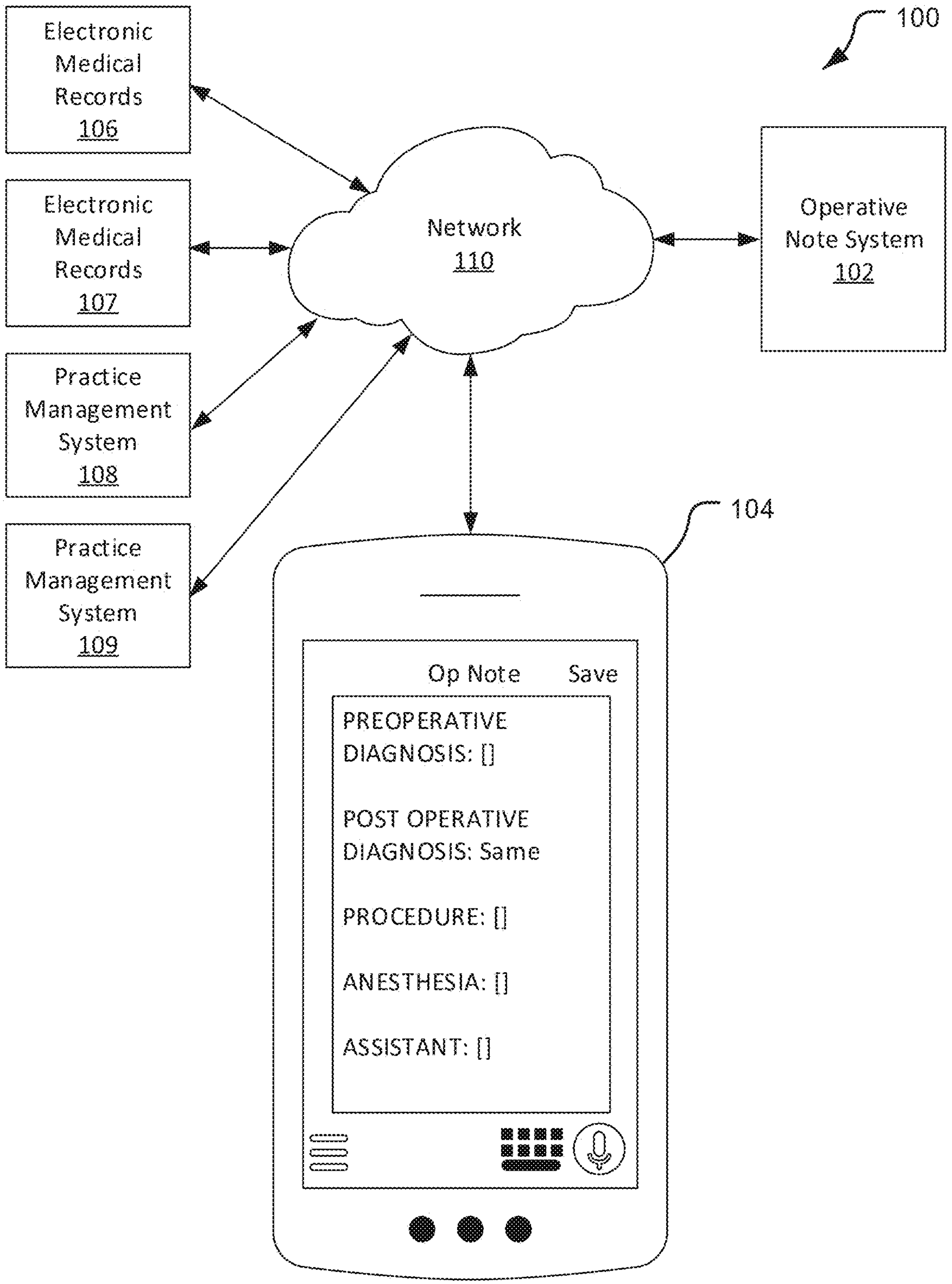
FIG. 1 illustrates an example operative note system and various systems in communication with the operative note system through a network, in accordance with various embodiments of the disclosure.

The operative note system and methods described herein allow a provider or user to use a mobile device or other computing device (e.g., a smartphone, wearable device, or laptop) to dictate operative notes related to an event and immediately review and sign off on the operative note. The event may relate to a specific surgery or procedure (identifiable by the time, place, type of surgery, etc.) for a particular patient (identifiable by a name, patient number, etc.) with an electronic medical record. The system may retrieve or receive additional information related or tied to the event, such as images from the event and bar codes of items used during the event. The system provides access to electronic medical records, practice management systems, and the like to both directly pull information for the operative note and transmit completed operative notes directly from the provider device to, for example, the patient's medical record. For example, a provider may be able to quickly view cases for which an operative note has not yet been generated, dictate the operative note, sign the operative note, and transmit the note to the patient's medical record from the provider's personal device, reducing inefficiencies present using other technologies. Further, the system may allow the provider to immediately populate an operative note with information from the patient's medical record. Likewise, the system may allow the provider to immediately or automatically populate an operative note with information, such as standard language for a specific type of surgery or procedure, from practice management systems, stored templates, and the like. In some examples, the provider may further be able to use the system to generate operative notes for cases associated with multiple facilities or provider groups, reducing the provider's workload and reducing errors that may be caused by delays and manual steps involved in providing operative notes to multiple systems manually.

The operative note system and methods described herein allow a provider to use optical devices or instruments to scan and/or capture images and immediately or automatically populate the operative note with the images and/or information related to the images. For example, a provider may be able to capture images during an event (e.g., a surgery or procedure) and automatically upload the images to a cloud computing platform or other storage location. The operative note system may then append (e.g., add as an attachment and/or embed within) the operative note with the images from the storage location and transmit the note to the patient's medical record, enhancing privacy by securely populating the note with images and reducing image transmission via multiple and unsecured devices. Additionally, since the images or information related to the scanned images are immediately or automatically added to the operative note, the delays associated with adding the images or information days or weeks after the procedure are reduced. Thus, the immediate generation of operative notes allows for efficiencies in other systems. For example, because the operative note may be completed on the same day as the procedure the operative note is related to, the healthcare provider may bill out faster than if the operative note was finalized days or weeks after the procedure. Additionally, since the operative note is generated quicker than days or weeks after the procedure, the operative note may be more accurate, e.g., may include correct codes and confirmation between scheduling and billing. In other examples, the provider may be able to view images associated with a procedure when dictating the operative note, also resulting in a more accurate operative note compared to systems where providers are not able to view such images when dictating and/or reviewing an operative note.

In some examples, a provider may be able to scan an image such as a barcode related to an implant (e.g., replacement joints, plates or screws, stents, and the like) or other surgical materials (e.g., sutures, catheters, and the like) used in a surgery or procedure, upload the image to the cloud or another network storage location, retrieve information related to the implant or surgical material (e.g., serial number, manufacturer information, etc.), automatically populate the operative note with the information, and transmit the note to the patient's medical record from the provider's personal device, reducing inefficiencies present using other technologies.

In other examples, another member of a surgical team (e.g., a nurse or medical assistant) may scan the implant or other surgical materials. Additionally, any device with access to the operative note system may be used to scan images from the event, e.g., a device other than the provider's personal device. For example, a nurse may use a camera in an operating room to scan or capture an image (e.g., a label, barcode, QR code, or the like) related to a catheter used in a surgery or procedure and automatically upload the image to a network storage location. The operative note system may then automatically populate the operative note with information related to the catheter. Further, a provider or other member of a surgical team may input or upload information related to an implant or other surgical materials used in a surgery or procedure in ways other than scanning or capturing a related image. For example, a provider or other member of a surgical team may manually insert a serial number associated with an implant or surgical materials to retrieve information related to the implant or surgical materials. The operative note system may then append the operative note with the information and transmit the note to the patient's medical record. The provider or other member of the surgical team may obtain the information in other ways, such as by searching a database using information about the manufacturer of the implant, obtaining the information from a database storing templates with the information, or other methods. Because a provider may generate an operative note immediately after completion of a surgery or procedure, the operative note system may reduce provider workload by allowing the provider to generate an immediately available operative note instead of hand writing an IPON and later dictating an operative note.

Various embodiments of the present disclosure will be explained below in detail with reference to the accompanying drawings. Other embodiments may be utilized, and structural, logical and electrical changes may be made without departing from the scope of the present disclosure. Turning now to the drawings, FIG. 1 illustrates an example operative note system 102 and various systems in communication with the operative note system 102 through a network 110, in accordance with various embodiments of the disclosure. The operative note system 102 may be generally implemented by a computing device or combinations of computing resources in various embodiments. In various examples, the operative note system 102 may be implemented by one or more servers, cloud computing resources, and/or other computing devices. The operative note system 102 may, for example, utilize various processing resources to generate dictation interfaces, access surgical cases, communicate with medical management systems, and the like. The operative note system 102 may further include memory and/or storage locations to store program instructions for execution by the processor and various data utilized by the operative note system 102.

Electronic medical records 106, 107 and practice management systems 108, 109 may similarly be implemented by one or more computing devices or combinations of computing resources in various embodiments. Electronic medical records 106, 107 and practice management systems 108, 109 may be medical management systems utilized by a clinic, surgical center, provider group, insurance company, or other organization for management of various tasks such as scheduling, maintaining patient medical records, and the like. The EMRs 106 and 107 may be different, meaning, for example, that the EMR 106 may be used by a different medical group and may use different software with different structures (e.g., fields and APIs used to communicate with the EMR 106) than the EMR 107. Similarly, the practice management systems 108 and 109 may be different systems used by different facilities, use different software, and the like. Accordingly, the operative note system 102 may obtain information (e.g., schedules, procedures, cases) for a provider across provider groups. In various examples, the operative note system 102 may communicate with additional medical management systems and various entities using the network 110.

The network 110 may be implemented using one or more of various systems and protocols for communications between computing devices. In various embodiments, the network 110 or various portions of the network 110 may be implemented using the Internet, a local area network (LAN), a wide area network (WAN), and/or other networks. In addition to traditional data networking protocols, in some embodiments, data may be communicated according to protocols and/or standards including near field communication (NFC), Bluetooth, cellular connections, and the like.

In various implementations, the provider device 104 and/or additional user devices may be implemented using any number of computing devices including, but not limited to, a computer, a laptop, tablet, mobile phone, smart phone, wearable device (e.g., AR/VR headset, smart watch, smart glasses, or the like), smart speaker, vehicle (e.g., automobile), or appliance. A user may be the provider or a person associated with the health care service, e.g., a member on the surgical team. The user may use the user device. The user device may be similar to or the same as the provider device 104. Generally, the provider device 104 and/or other user devices may include one or more processors, such as a central processing unit (CPU) and/or graphics processing unit (GPU). The user devices 104 may generally perform operations by executing executable instructions (e.g., software) using the processor(s). For example, a provider device 104 may be a tablet, camera, or other mobile or computing device in an operating room associated with an event and a provider may capture images or accept other data inputs related to the event. The provider device 104 may execute instructions using a processor to send the captured images or data to a server, e.g., a cloud computing resource. The provider may later elect to append the captured images or additional data or information to an operative note related to the event or the operative note system 102 may automatically add the captured images to the operative note system.

Components of the operative note system 102 and in communication with the operative note system 102 shown in FIG. 1 are exemplary and may vary in some embodiments. For example, in some embodiments, the operative note system 102 may be distributed across multiple computing elements, such that components of the operative note system 102 communicate with one another through the network 110. Further, in some embodiments, computing resources dedicated to the operative note system 102 may vary over time based on various factors such as usage of the operative note system 102.

Figure 2:
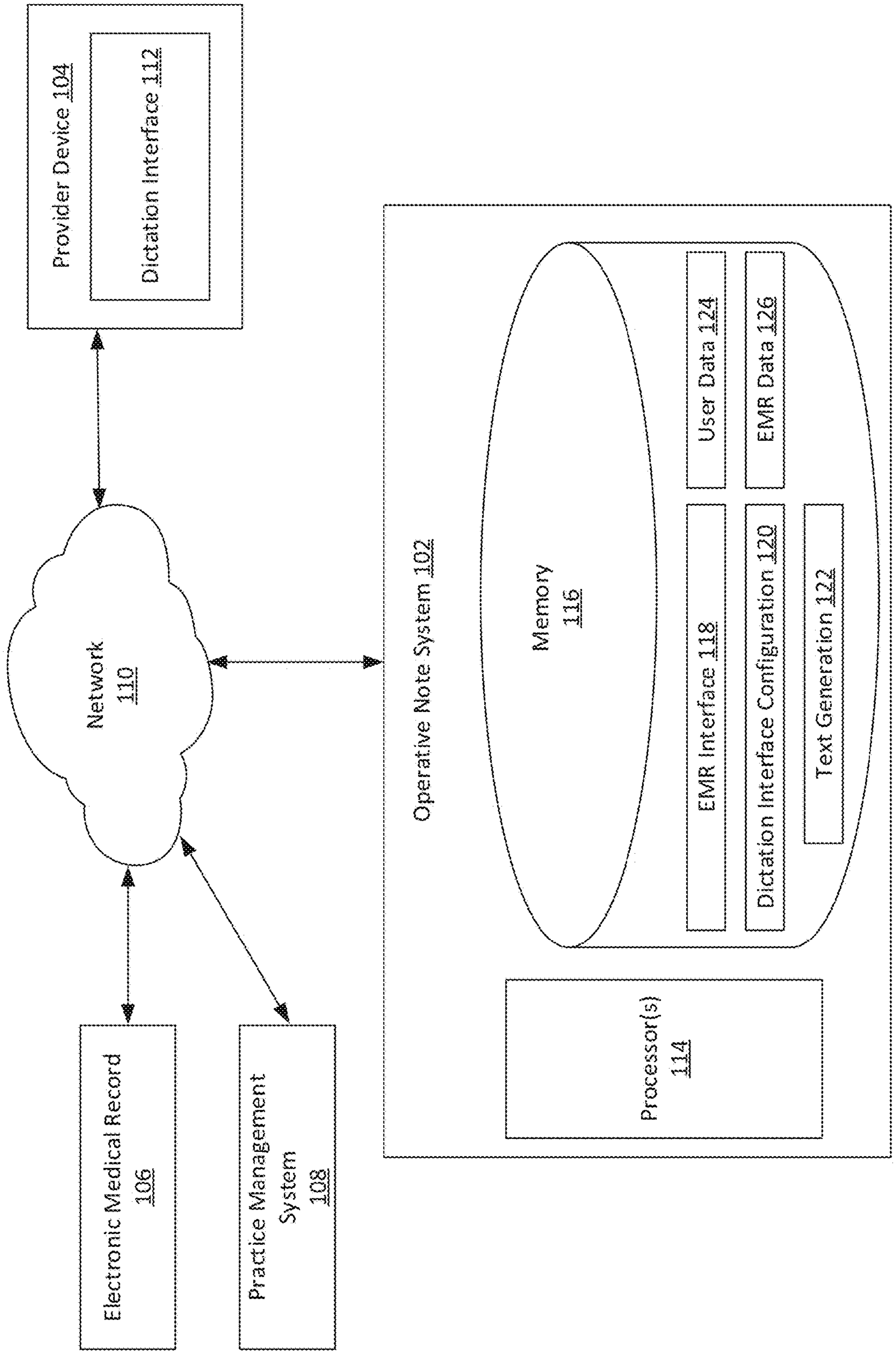
FIG. 2 illustrates an example operative note system in accordance with various embodiments of the disclosure.

FIG. 2 illustrates an example operative note system 102 in accordance with various embodiments of the disclosure. The operative note system 102 may be in communication with other services, components, and systems through a network 110. For example, the operative note system 102 may communicate with a provider device 104 through the network 110 to provide a dictation interface 112 at the provider device 104 for generating operative notes. Additionally, the operative note system 102 may append or add images captured by the provider device 104, for example, to an operative note related to the event. Appending and adding an image or information may include adding the image or information as an attachment that is separate but related to the operative note or embedding the image or information within the operative note. The images may be captured by any device with access to the operative note system 102, such as a camera, optical scanner, medical imaging device (e.g., ultrasound probe), and the like.

The operative note system 102 is interoperable with and between the practice management systems 108 and 109 and electronic medical records 106 and 107. For example, the operative note system 102 may send data (e.g., generated operative notes) to and receive data from various medical management systems via the network 110, including the practice management systems 108 and 109 and the electronic medical records 106 and 107. For example, the operative note system 102 may receive patient data (e.g., name, age, and other data), event data (e.g., type of procedure, diagnosis codes, and the like) from the practice management systems 108 and 109 and/or the electronic medical records 106 and 107. In some examples, the operative note system 102 may be in communication with, or integrated into, the Surgical Coordination System described in related U.S. Non-Provisional application Ser. No. 17/818,257 filed Aug. 8, 2022, entitled "Coordinated Processing and Scheduling for Surgical Procedures." The above application is hereby incorporated by reference herein in its entirety.

In various implementations, the operative note system 102 may include or utilize one or more hosts or combinations of compute resources, which may be located, for example, at one or more servers, cloud computing platforms, computing clusters, and the like. Generally, the operative note system 102 is implemented by compute resources including hardware for memory 116 and one or more processors 114. For example, the operative note system 102 may utilize or include one or more processors, such as a CPU, GPU, and/or programmable or configurable logic. In some embodiments, various components of the operative note system 102 may be distributed across various computing resources, such that the components of the operative note system 102 communicate with one another through the network 110 or using other communications protocols. For example, in some embodiments, the operative note system 102 may be implemented as a serverless service, where computing resources for various components of the operative note system 102 may be located across various computing environments (e.g., cloud platforms) and may be reallocated dynamically and/or automatically according to, for example, resource usage of the operative note system 102. In various implementations, the operative note system 102 may be implemented using organizational processing constructs such as functions implemented by worker elements allocated with compute resources, containers, virtual machines, and the like.

The memory 116 may include instructions for various functions of the operative note system 102 which, when executed by processor 114, perform various functions of the operative note system 102. The memory 116 may further store data and/or instructions for retrieving data used by the operative note system 102. Similar to the processor 114, memory resources utilized by the operative note system 102 may be distributed across various physical computing devices. In some examples, memory 116 may access instructions and/or data from other devices or locations, and such instructions and/or data may be read into memory 116 to implement the operative note system 102.

The memory 116 may store user data 124 which may, in various examples, be used by the operative note system 102 to generate user interfaces, generate operative notes, authenticate users and/or user devices 104, and the like. User data 124 may include information specific to a provider or other user of the operative note system 102. For example, user data 124 may include information about practice management systems 108 and 109 associated with a provider. A practice management system 108 or 109 may be associated with a provider when the provider is affiliated with a practice using the practice management system 108 or 109. In various examples, a provider may be associated with multiple practice management systems (e.g., both practice management system 108 and practice management system 109) such as systems used by clinics, surgical centers, and the like. Information about practice management systems 108 and 109 may include query information for retrieving provider schedules, appointment or case status, and other data from practice management systems 108 and 109 associated with the provider or surgeries performed by the provider. Query information may include for example, a provider identifier used to query practice management systems 108 and 109, cases associated with the provider, schema data for management systems 108 and 109, and other data used to generate and send queries and/or information (e.g., finalized operative notes) to practice management systems 108 and 109.

In some examples, user data 124 may further include descriptions of a surgery or procedure and/or descriptions of surgical tools or materials used in or associated with an event. For example, user data 124 may include standard vocabulary or stock language generally used in relation to a specific type of surgery or procedure. Additionally, user data 124 may include information related to a tool or device used during a surgery, e.g., a serial number for and manufacturer information of an implant used in a knee replacement surgery. The operative note system 102 may receive user data 124 (e.g., standard vocabulary, stock language, default descriptions, or defined texts related to a specific type of event) and populate sections of an operative note with the data. Further, such user data 124 may be used by the operative note system 102 to, for example, generate templates for operative notes, populate the template with stock language and the like. For example, the operative note system 102 may automatically select a template to be populated based on the user data 124 containing descriptions of the surgery or procedure. Additionally, the dictation interface 112 may provide templates partially populated with automatically received user data 124 such as stock language for specific types of surgeries and procedures. Information regarding descriptions of a surgery or procedure and/or descriptions of surgical tools or materials used in or associated with an event may be stored at another storage location accessible by the operative note system 102, e.g., not stored as user data 124 in the memory 116.

In some examples, user data 124 may further include hardware settings and/or configurations associated with a user device 104. For example, user data 124 may include preferences regarding microphone volume and/or sensitivity, display settings (e.g., text size), and other settings applicable to a user or a type, brand, model, or other group of user device 104. User data 124 may further include various settings, preferences, and the like associated with a user or group of users. For example, such settings and preferences may be selected and/or applied to an individual provider or may be selected and applied to groups of users, such as users associated with a clinic, surgical center, specialty, or other grouping. Such user data 124 may be used by the operative note system 102 to, for example, generate templates for operative notes, populate the template with stock language, generate text of operative notes responsive to audio input received at a provider device 104, generate user interfaces at the provider device 104 and the like.

Settings and/or preferences stored as user data 124 may include templates for operative notes. Templates may include template text (e.g., field headings or identifiers included in an operative note), selectable fields, and/or fields populated from other sources, such as by query to a practice management system 108 or 109 and/or an EMR 106 or 107. Such templates may be configured for particular procedures (e.g., may include standard vocabulary related to the procedure), for an individual provider, for a group of providers (e.g., those associated with a surgical center, provider group, or the like), or other subset of cases or users. In some examples, providers in a provider group may use templates associated with the provider group and/or may revise all or portions of the provider group template. For example, a provider group template may include required fields for the provider group and an individual provider may have access or permission to add additional fields and/or edit some fields in the provider group template.

For example, FIG. 12 illustrates an example template 1100 for an operative note. The template 1100 may be generic, e.g., it may be customized for a variety of procedures. Various fillable fields of the template 1100 may be populated by the operative note system 102 by obtaining information from an EMR 106 or 107, practice management system 108 and/or 109, and/or from user data 124. For example, patient ID, preoperative diagnosis, and procedure may be obtained from an EMR 106 associated with the patient. In some examples, date of surgery, assistant, and/or other fields may be populated with information from a practice management system 108 (e.g., a scheduling system for a surgery center) and the surgeon field may be populated from the user data 124 associated with the provider.

Other dictation templates may be specific to types of procedures. For example, FIG. 13 illustrates an example dictation template 1200 used for carpal tunnel release. Similar to the template 1100, fields of the template 1200 may be populated by information obtained from an EMR 106, practice management system 108, user data 124, and/or other locations. For example, the template 1200 includes text (e.g., stock language) narrating a typical procedure. In some examples, the provider may select text provided in the template 1200 to edit the text to reflect the course of the procedure.

In another example, FIG. 14 illustrates an example dictation template 1300 used for left Achilles tendon repair. The dictation template 1300 may, like the template 1200, be provided at the provider device 104 responsive to a voice shortcut or may be automatically provided for generation of operative notes for left Achilles tendon repair. The dictation template 1300 includes additional fields within the text which may be populated by information obtained from an EMR 106, practice management system 108, user data 124, and/or other locations. For example, the provider may use the provider device 104 to scan a bar code on an implant device or other surgical material. The operative note system 102 may access various locations providing data related to the implant device or other surgical material, such as a serial number or manufacturer information, to the additional fields in the template 1300. Some of these fields may be linked to one another. For example, the operative note text includes several fields where a provider may select the appropriate pronouns for a patient. In some examples, such fields may be populated (e.g., the correct pronouns chosen) based on the patient's information in, for example, the EMR 106. Fields for patient age may be similarly populated. As with the dictation template 1200, a provider may insert or delete text and/or images from the template 1300 to reflect the course of the surgery or procedure. For example, the provider may capture images from an event on a provider device 104 and insert the captured images into the template 1300. The provider may review the captured images, which may be automatically appended to the operative note via the operative note system 102, such that the images may be included in the operative note transmitted to the EMR 106, 107. Such images may then be used by the provider to monitor the patient's progression post-surgery. Additionally, the provider may scan a bar code on an implant device from an event using the provider device 104, and instead of the template 1300 being automatically populated, the provider may later retrieve data related to the implant device and selectively insert the data into the template 1300. In various examples, the templates 1200, 1300, and other procedure specific templates may include additional text and/or fields as desired.

Additional settings and preferences may include shortcuts used in dictation. As with operative note templates, dictation shortcuts may be configured for or by an individual provider, a group of providers, provided as default shortcuts, used with particular procedures, etc. A dictation shortcut may, in some examples, cause the operative note system 102 to retrieve specific information from a practice management system 108 or 109, an EMR 106 or 107, or other source and populate an operative note with the retrieved information responsive to receipt of the shortcut. For example, a dictation shortcut may cause the operative note system 102 to retrieve a preoperative diagnosis from an EMR 106 or 107 when a user says "pre-op diagnosis" into the user device 104. Dictation shortcuts may, in some examples, cause the operative note system 102 to populate an operative note with defined text responsive to receipt of the shortcut. Such defined text may include single words or phrases (e.g., spelling out postoperative responsive to the user saying "post-op" into the user device 104) and or longer defined text, such as sentences and paragraphs. For example, a user may say "normal procedure" into the user device 104, and the operative note may be populated with a default description of the procedure. In some examples, the default description may include fields, editable text, and the like in addition to default text.

Example dictation shortcuts may insert text into an operative note and/or may perform other functions at the user device 104. For example, "insert patient name," "patient name," "insert patient first name," and "insert patient last name" may insert the patient's name (or the desired portion of the patient's name) into an operative note. Other dictation shortcuts, such as "prefill form," "prefill appointment," and "prefill visit" may fill a template with default values. Some shortcuts, such as "clear form," "clear appointment," and "clear visit" may remove information from a template or dictation interface. Some dictation shortcuts may also save, finalize, transmit, close, or perform other operations for an operative note or addendum. For example, dictation shortcuts may include "save addendum," "close addendum," "save dictation," "save form," "save appointment," "save visit," "complete form," "complete appointment," "sign off appointment," "sign off dictation," "complete visit," "complete dictation," and "accept form defaults."

In some examples, dictation shortcuts may be used to populate a blank dictation interface with a dictation template. For example, a provider may say "insert left Achilles tendon repair" to populate a blank dictation interface with the dictation template 1300 specific to left Achilles tendon repair. In some examples, such a dictation shortcut may replace other contents of the dictation interface (e.g., a generic dictation template 1100) with the dictation template 1300.

Memory 116 may further store EMR data 126 which may be used by the operative note system 102 to, for example, populate user interfaces, generate operative notes, send completed operative notes to an EMR 106 or 107, and the like. EMR data 126 may, in various embodiments, include information and data used to query the EMRs 106 and 107 and/or other medical management systems in communication with the operative note system 102. For example, EMR data 126 may include schema and fields of the EMR 106 and the EMR 107 including, in some examples, mapping of EMR fields to case data, fields of operative notes (including text of operative note templates), dictation shortcuts, and the like. In some examples, where user data 124 includes an audio shortcut to populate an operative note with a patient's full name when a user says "patient name," the EMR data 126 may include template queries, schema mappings, or other information used to retrieve a patient's full name from an EMR 106. In another example, user data 124 may include templates for operative notes, where some information in the template is populated from data in an EMR 106 or 107. For example, a template may include fields for patient name, pre-operative diagnosis, patient identifier, and the like, which may be populated by identifying fields holding the desired information in an EMR 106 or 107 and querying the identified field for the data to populate the template. Accordingly, EMR data 126 may include similar template queries, schema mappings, or additional information used to retrieve such data from the EMR 106. In various embodiments, EMR data 126 may also include information used to send data to the EMRs 106 and 107, including for example, an operative note generated using the operative note system 102.

The memory 116 may include instructions implementing the EMR interface 118. The EMR interface 118 may communicate with one or more EMRs 106 and 107 and other modules and/or processes of the operative note system 102 to communicate information to the EMRs 106 and 107 and retrieve information from the EMRs 106 and/or 107. For example, the EMR interface 118 may access EMR data 126 to query the EMR 106 for patient information to generate an operative note, display a user interface including the patient information, and the like. Further, the EMR interface 118 may use EMR data to communicate a finalized and signed operative note generated using the operative note system 102 to the EMR 106.

In some examples, the EMR interface 118 may further include functionality for authenticating users (e.g., to give a user access to information at the EMR 106). To authenticate a user device 104, the EMR interface 118 may, for example, receive user login information corresponding to an EMR 106 (e.g., a username, password, biometric data, or other identifier) and transmit the information to the EMR 106 to authenticate the user. The EMR interface 118 may, in some examples, communicate with additional authentication services to authenticate a user and, upon receiving an authentication from the authentication service, connect the user device 104 to the operative note system 102 and the EMR 106.

In some examples, the EMR interface 118 may include functionality for identifying an EMR to query for a specific case (e.g., for generation of an operative note). For example, a user device 104 in communication with the operative note system 102 may be associated with a user (e.g., a provider) associated with several groups, where one group utilizes the EMR 106 and another group utilizes the EMR 107. Accordingly, the EMR interface 118 may determine whether to query the EMR 106 or the EMR 107 to obtain information for a particular case and/or to transmit a finalized operative note. In some examples, the EMR interface 118 may query multiple EMRs in association with one user interface or operative note of the operative note system 102. For example, a provider may request to view all cases ready for operative note generation and associated with the provider. The cases presented to the provider may include cases performed, for example, at different facilities or through different provider groups using different EMRs.

The memory 116 further includes instructions implementing dictation interface configuration 120. Dictation interface configuration 120 may communicate with the EMR interface 118 and may use user data 124 to generate and/or present a dictation interface at a user device 104. A dictation interface may be a user interface displayed at the user device 104 including elements allowing the user to generate an operative note by dictation (e.g., by speaking the text of the operative note) at the user device 104. Dictation interface configuration 120 may include functionality to, for example, identify and render a dictation template as part of a dictation interface, populate various fields of a dictation template, apply various user settings (e.g., from user data 124), link the user device 104 to a dictation service or model, and the like. In some examples, responsive to a request for a dictation interface associated with a particular case or procedure, dictation interface configuration 120 may reference user data 124 to locate a dictation template applicable to the case or procedure and/or the provider generating the operative note. Dictation interface configuration 120 may further populate fields of the chosen dictation template by, for example, communicating with the EMR interface 118 to query the EMR 106 for the information to populate the fields of the dictation template.

Instructions for implementing text generation 122 may further be stored at the memory 116. Text generation 122 may include, in some examples, an interface to one or more external dictation systems or services. For example, text generation 122 may provide an interface between dictation interface configuration 120 and a dictation service such as DRAGON®. In these examples, text generation 122 may communicate audio input to the dictation service and return text to dictation interface configuration 120 for display at the user device 104. Text generation 122 may, in some examples, include dictation models within the operative note system 102. For example, the operative note system 102 may include neural networks or other machine learning models trained to receive audio input and produce text corresponding to the audio input. Such models may, in some examples, be tuned over time for accuracy for particular users. Additionally, the models may be trained on specific vocabulary more likely to appear in operative notes or may be otherwise trained for use in medical settings.

In some examples, the memory 116 may include additional instructions implementing additional features of the operative note system 102 not described above. For example, the operative note system 102 may communicate with authorization services, workflow tracking services, and/or other services to generate operative notes, securely send operative notes and other protected information, and perform other functions. For example, the operative note system 102 may generate the operative note as a portable document format (PDF). The operative note system 102 may automatically populate sections of the PDF. For example, the operative note system 102 may automatically populate a header section with the name of the type of procedure. The PDF operative note may include a time stamp, which may be for managerial purposes such as auditing. The PDF operative note may include images or information related to images captured during the procedure. The operative note system 102 may generate multiple PDFs related to the procedure, e.g., a PDF operative note and separate PDFs containing images or information related to images captured during the procedure.

Figure 3:
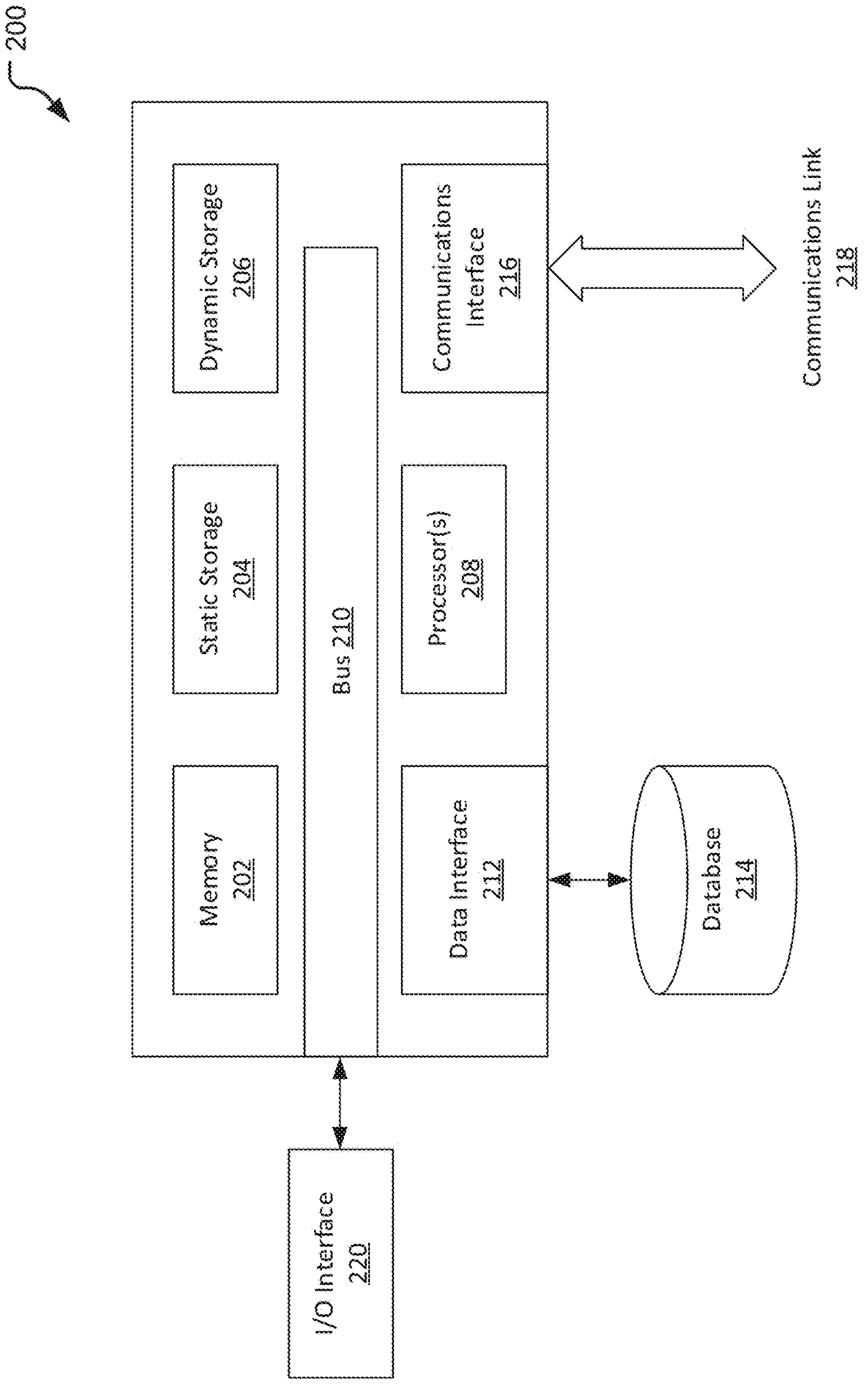
FIG. 3 is a schematic diagram of an example computer system implementing various embodiments in the examples described herein.

The operative note system 102 may be implemented using various computing systems. Turning to FIG. 3, an example computing system 200 may be used for implementing various embodiments in the examples described herein. For example, processor 120 and memory 122 may be located at one or several computing systems 200. In various embodiments, user device 116 is also implemented by a computing system 200. Various medical management systems, such as clinic practice management 104, electronic medical records 106 and 107, and surgery center practice management 108 and 109 may also be implemented by one or several computing systems 200. This disclosure contemplates any suitable number of computing systems 200. For example, the computing system 200 may be a server, a desktop computing system, a mainframe, a mesh of computing systems, a laptop or notebook computing system, a tablet computing system, an embedded computer system, a system-on-chip, a single-board computing system, or a combination of two or more of these. Where appropriate, the computing system 200 may include one or more computing systems; be unitary or distributed; span multiple locations; span multiple locations; span multiple machines; span multiple data centers; or reside in a cloud, which may include one or more cloud components in one or more networks.

Computing system 200 includes a bus 210 (e.g., an address bus and a data bus) or other communication mechanism for communicating information, which interconnects subsystems and devices, such as processor 208, memory 202 (e.g., RAM), static storage 204 (e.g., ROM), dynamic storage 206 (e.g., magnetic or optical), communications interface 216 (e.g., modem, Ethernet card, a network interface controller (NIC) or network adapter for communicating with an Ethernet or other wire-based network, a wireless NIC (WNIC) or wireless adapter for communicating with a wireless network, such as a WI-FI network), input/output (I/O) interface 220 (e.g., keyboard, keypad, mouse, microphone). In particular embodiments, the computing system 200 may include one or more of any such components.

In particular embodiments, processor 208 includes hardware for executing instructions, such as those making up a computer program. The processor 208 circuitry includes circuitry for performing various processing functions, such as executing specific software for perform specific calculations or tasks. In particular embodiments, I/O interface 220 includes hardware, software, or both, providing one or more interfaces for communication between computing system 200 and one or more I/O devices. Computing system 200 may include one or more of these I/O devices, where appropriate. One or more of these I/O devices may enable communication between a person and computing system 200.

In particular embodiments, communications interface 216 includes hardware, software, or both providing one or more interfaces for communication (such as, for example, packet-based communication) between computing system 200 and one or more other computer systems or one or more networks. One or more memory buses (which may each include an address bus and a data bus) may couple processor 208 to memory 202. Bus 210 may include one or more memory buses, as described below. In particular embodiments, one or more memory management units (MMUs) reside between processor 208 and memory 202 and facilitate accesses to memory 202 requested by processor 208. In particular embodiments, bus 210 includes hardware, software, or both coupling components of computing system 200 to each other.

According to particular embodiments, computing system 200 performs specific operations by processor 208 executing one or more sequences of one or more instructions contained in memory 202. For example, instructions for the management system interface 124 and user interface configuration 126 may be contained in memory 202 and may be executed by the processor 208. Such instructions may be read into memory 202 from another computer readable/usable medium, such as static storage 204 or dynamic storage 206. In alternative embodiments, hard-wired circuitry may be used in place of or in combination with software instructions. Thus, particular embodiments are not limited to any specific combination of hardware circuitry and/or software. In various embodiments, the term "logic" means any combination of software or hardware that is used to implement all or part of particular embodiments disclosed herein.

The term "computer readable medium" or "computer usable medium" as used herein refers to any medium that participates in providing instructions to processor 208 for execution. Such a medium may take many forms, including but not limited to, nonvolatile media and volatile media. Non-volatile media includes, for example, optical or magnetic disks, such as static storage 204 or dynamic storage 206. Volatile media includes dynamic memory, such as memory 202.

Computing system 200 may transmit and receive messages, data, and instructions, including program, e.g., application code, through communications link 218 and communications interface 216. Received program code may be executed by processor 208 as it is received, and/or stored in static storage 204 or dynamic storage 206, or other storage for later execution. A database 214 may be used to store data accessible by the computing system 200 by way of data interface 212. For example, case data 128, medical management system data 130, and/or workflow data 132 may each be stored using a database 214. In various examples, communications link 218 may communicate with, for example, user devices to display user interfaces to the surgical coordination system 102.

Figure 4:
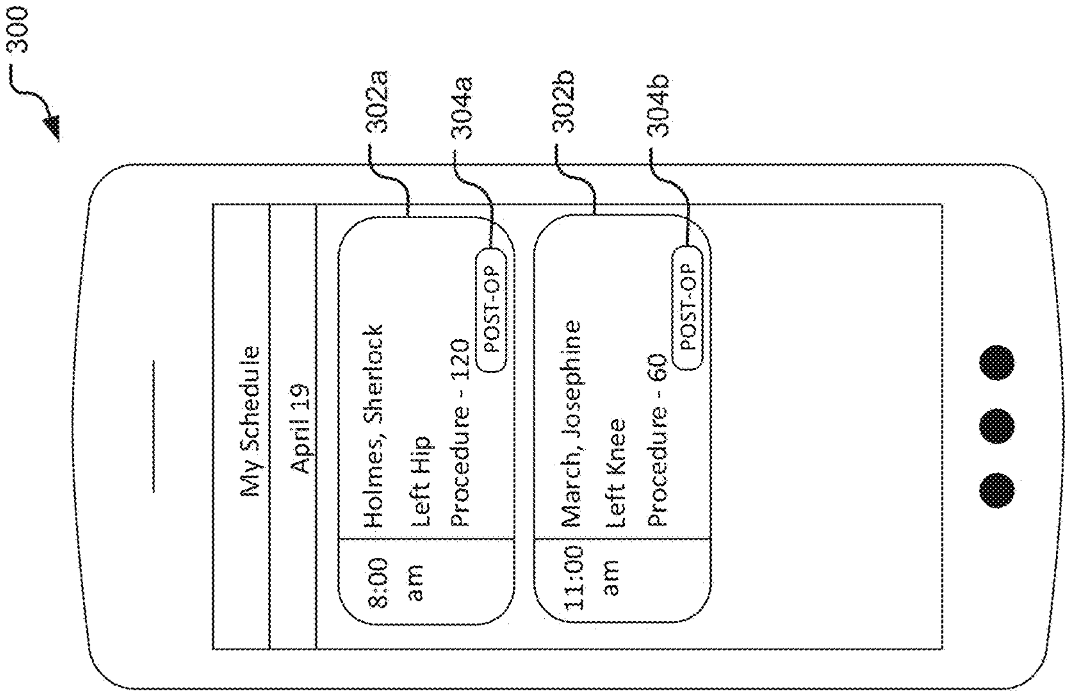
FIG. 4 illustrates an example user interface displaying surgical cases associated with a provider, in accordance with various embodiments of the disclosure.

FIG. 4 illustrates an example user interface 300 displaying events, also referred to herein as cases (e.g., surgical cases), associated with a provider, in accordance with various embodiments of the disclosure. The user interface 300 may be displayed at a provider device 104 after the provider device 104 has established communication with and has been authenticated by the operative note system 102. The user interface 300 displays cases 302*a* and 302*b* associated with a provider and a date. Each of the cases 302*a* and 302*b* have associated statuses 304*a* and 304*b*, respectively.

In various examples, the user interface 300 may be generated responsive to a request by the provider (e.g., using the provider device 104) to view a listing of cases associated with the provider. A case may be associated with a provider when the provider is scheduled to perform or has performed the surgery or one or more procedures included in the case. Such cases may, in some examples, be only cases which are available for operative note generation (e.g., cases where the patient has already undergone the associated surgery and/or procedure). In some examples, a provider may view all cases associated with the provider, regardless of status. The cases may be associated with various medical groups (e.g., performed with multiple surgical centers or other facilities). While the cases shown in the user interface 300 are displayed as cases which were scheduled on a single day, the user interface 300 may be configured to display cases over a selected week, range of dates, or other periods of time. Further, in some examples, the user interface 300 may show a listing of all cases available for generation of an operative note, regardless of the date or dates associated with the case. In some examples, the cases may be filtered or ordered based on criteria provided with the provider request. For example, the most recent cases may be displayed after older cases. In some examples, the cases may be grouped by procedure type, patient, facility, and/or other criteria specified in the request.

Figure 5:
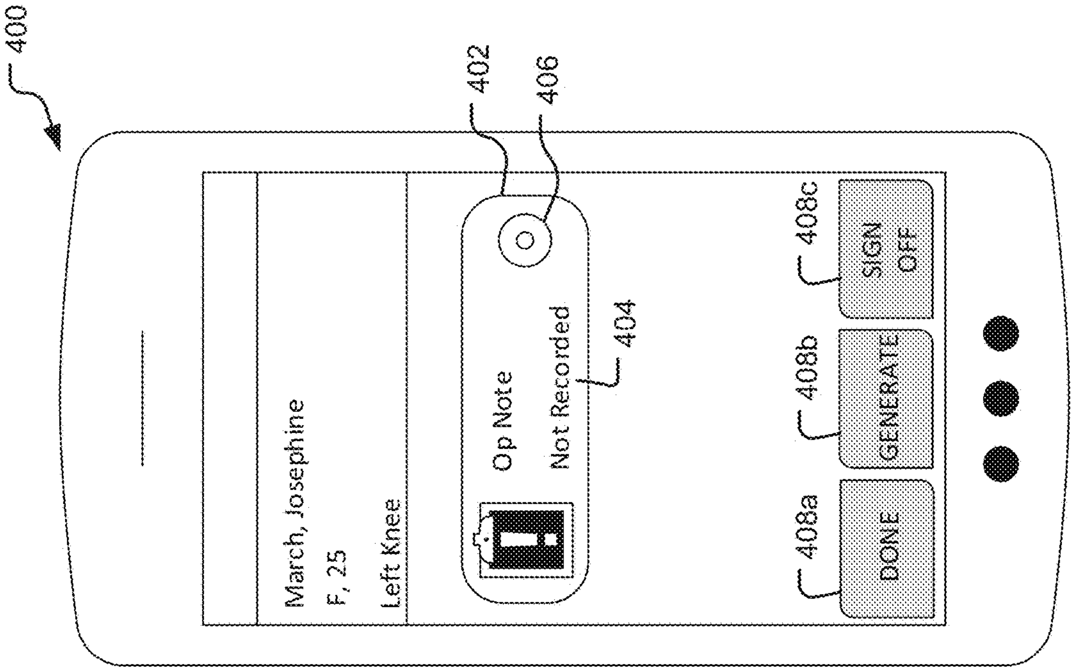
FIG. 5 illustrates an example user interface displaying a selected surgical case, in accordance with various embodiments of the disclosure.

The surgical case elements 302*a* and 302*b* may each be selectable (e.g., by touch, gesture, mouse click, or other method). Selecting a surgical case element may display additional information about the surgical case and/or may prompt generation of additional interfaces. For example, selection of the surgical case element 302*b* may cause the operative note system 102 to generate and display a user interface 400, illustrated in FIG. 5, at the provider device 104.

The user interface 400 shows additional information about the surgical case represented by the case element 302*b*, including an element 402 specific to the status of an operative note associated with the case. In some examples, the user interface 400 may include additional elements showing the status of other tasks, notifications, and the like associated with the case. The operative note element 402 may include a status 404, showing in the user interface 400 that the operative note has not been recorded. Other statuses may be displayed for operative notes which have been recorded but not finalized, finalized but not signed off, signed off without being sent to, for example the EMR 106 and/or a practice management system 108, and finalized, signed off, and sent to other systems.

The element 402 further includes a recording control 406 which may, in some examples, vary in appearance and functionality based on the status 404 of the operative note. For example, the recording control 406 may, when the status 404 is "Not Recorded" appear as a recording icon and may, when selected, prompt generation of a dictation interface to record the operative note. When, for example, the status reflects that the operative note has been finalized, the recording control 406 may be rendered as an arrow and, when selected, prompt generation of the finalized operative note with the option to, for example, add an addendum or captured images from the event or related to the event (e.g., pre-procedure imaging) to the operative note. Elements 408*a*, 408*b*, and 408*c* may likewise be rendered and may function differently based on the status 404 of the operative note. For example, where the status is "Not Recorded," the elements 408*a*, 408*b*, and 408*c* may be grayed out or otherwise not selectable, as the operative note has not been generated. Where the status reflects that the operative note has been recorded but not finalized, the elements 408*a*, 408*b*, and 408*c* may allow the user to sign off on the operative note, generate the operative note, and mark the case as done.

Figure 6:
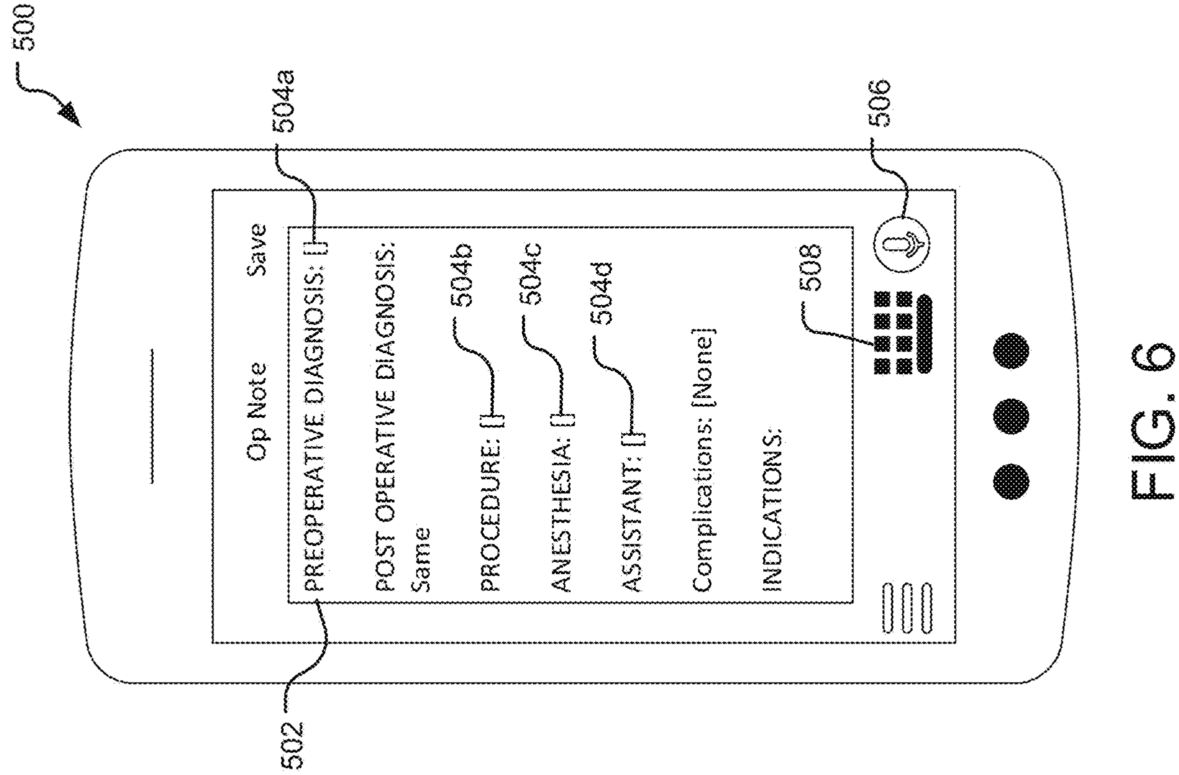
FIG. 6 illustrates an example dictation interface presented at a provider device, in accordance with various embodiments of the disclosure.

FIG. 6 illustrates an example dictation interface 500 presented at a provider device, in accordance with various embodiments of the disclosure. The dictation interface 500 may be rendered at the user device 104 responsive to, for example, selection of the recording element 406 in the user interface 400. The dictation interface 500 generally includes one or more selectable fields 504*a*-504*d* which, when selected allow the user to enter text into the dictation interface 500 through speaking into the user device 104 and/or, in some examples, typing into the dictation interface. Dictation interfaces, including the dictation interface 500 may include template text 502, which may be rendered in the dictation interface 500 based on a dictation template. An audio element 506 may, when selected, allow the user to provide text for the operative note through dictation. A keyboard element 508 may, when selected, allow the user to provide text using a keyboard which may, in various examples, be attached to or in communication with the user device 104 or may be rendered on a touch screen display of the user device 104 along with the dictation interface 500. Additional elements may be displayed with the dictation interface 500 including, in various examples, options to sign off on the operative note, save the recorded operative notes, and the like.

Figure 7:
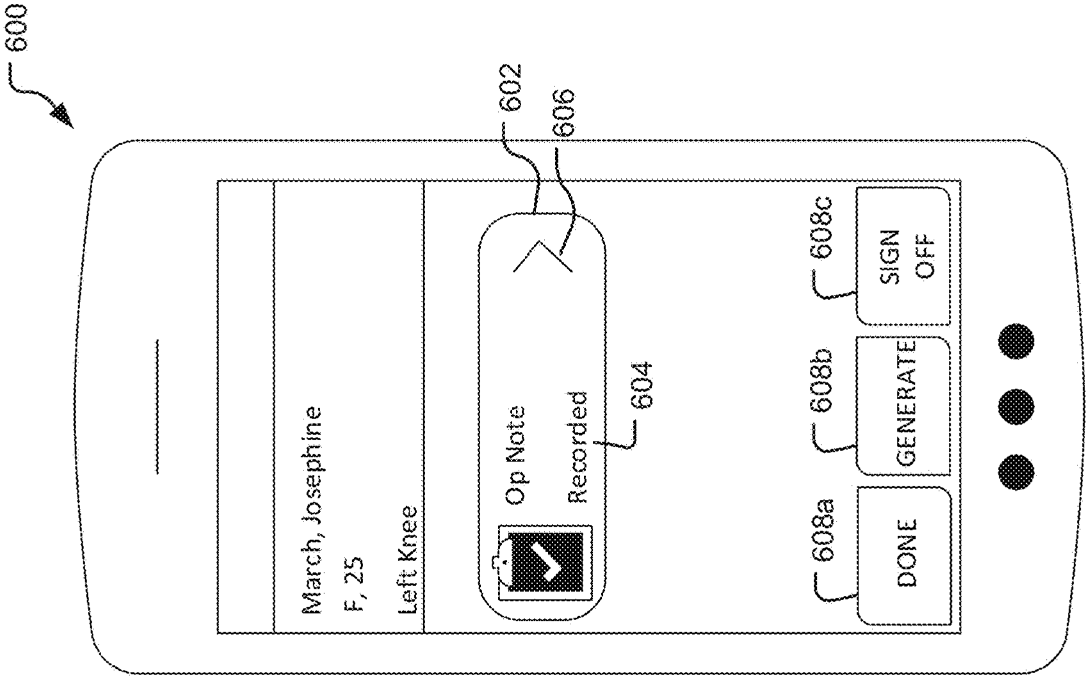
FIG. 7 illustrates an example user interface displaying a selected surgical case after recording an operative note, in accordance with various embodiments of the disclosure.

FIG. 7 illustrates an example user interface 600 displaying a selected surgical case after recording an operative note, in accordance with various embodiments of the disclosure. The user interface 600 includes an operative note element 602 showing a status 604 of an operative note for the selected case. The status 604 reflects that the operative note has been recorded. The operative note element 602 includes an element 606 which may be operative, when selected, to view and/or edit the recorded operative note. Elements 608*a*-608*c* may be selectable due to the status 604 of the operative note showing that an operative note has been recorded. For example, element 608*b* may, when selected, generate a draft of the recorded operative note for review. The generated operative note may be viewable at another interface of the provider device 104 and/or may be transmitted to another device or display in communication with the system 102. Element 608*c* may, when selected, allow the provider to sign off on the operative note. In some examples, selection of the element 608*c* may first generate the operative note for review and subsequent approval. For example, approval may be in the form of a signature. Approval may be in any form of authentication. For example, approval may be an input that indicates the operative note is approved (e.g., biometric input, such as the user pressing her thumb on a finger print reader, audio input, etc.). The operative note system 102 may, in some embodiments, automatically transmit the operative note to the EMR 106 and/or a practice management system 108 when the provider signs or otherwise approves the operative note.

Figure 8:
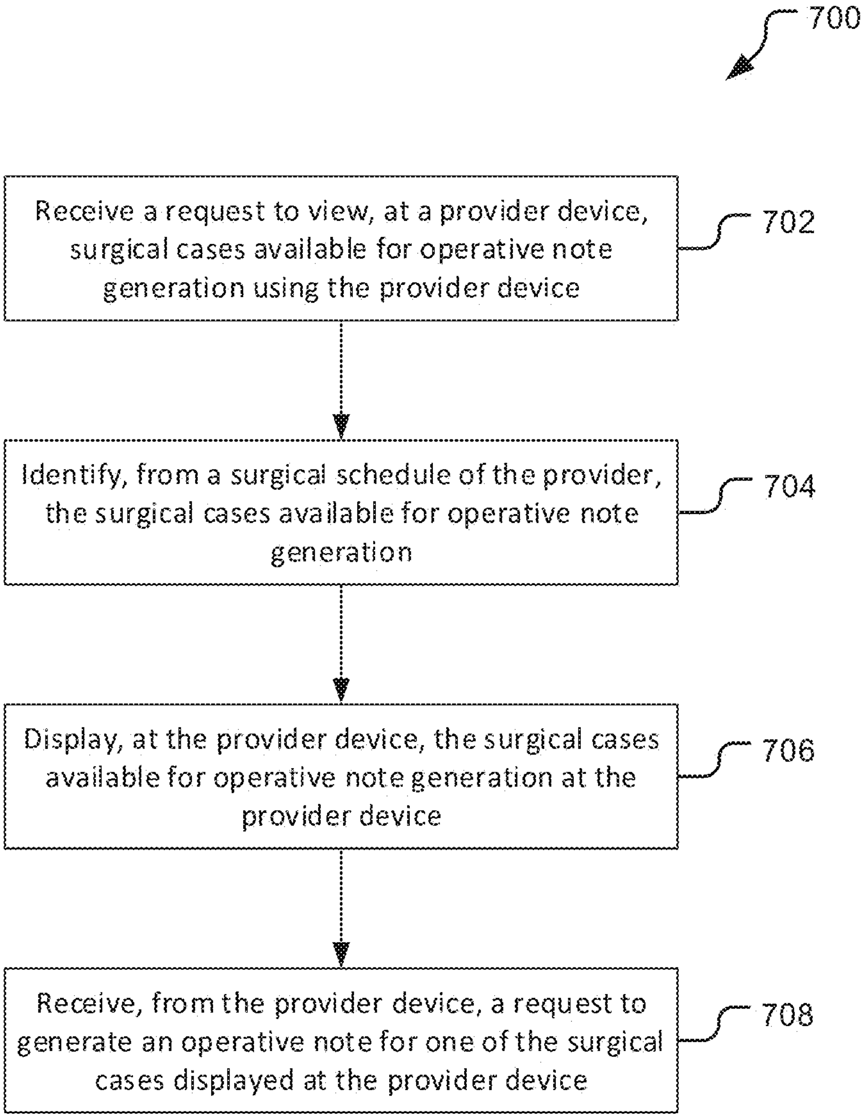
FIG. 8 illustrates example operations for generating a user interface at a provider device, in accordance with various embodiments of the disclosure.

FIG. 8 illustrates example operations 700 for generating a user interface at a provider device, in accordance with various embodiments of the disclosure. At block 702, the operative note system 102 receives a request to view, at a provider device 104, surgical cases available for operative note generation using the provider device 104. Generally, the request may be received through the display of the provider device 104, where the provider device 104 is in communication with the operative note system 102. In some examples, the provider device 104 may connect to the operative note system 102 through a web browser, mobile application, or the like, and the request may be transmitted via the web browser or mobile application used to connect to the operative note system 102. In some examples, the request may include additional information and/or parameters regarding which cases to view. For example, the request may include a date range of cases, one or more locations associated with cases (e.g., where a surgery and/or procedure was performed), patient or group of patients, types of procedures, and the like.

The operative note system 102 identifies, from a surgical schedule of the provider, the surgical cases available for operative note generation at block 704. To identify cases available for operative note generation, the operative note system 102 may use user data 124 and/or EMR data 126 to communicate with one or more practice management systems 108 and 109 and/or the electronic medical records 106 and 107. For example, the operative note system 102 may identify, based on the user data 124 associated with the provider device 104, one or more practice management systems 108 associated with the provider, along with a provider identifier associated with the provider for the respective practice management systems 108. The operative note system 102 may then query each of the respective practice management systems (e.g., using an API call or other structured query) for information about events (e.g., appointments and/or cases where and when, for example, the surgery and/or procedure has been completed).

Because the operative note system 102 may identify cases with completed procedures, a provider may be able to generate an operative note immediately after a procedure or surgery using their own provider device 104. For example, when the patient leaves the operating room, the provider may dictate an operative note, append captured images from the procedure, and insert data corresponding to bar codes scanned or other identifiers entered during the procedure from any location using the provider device 104, so that operative notes may be generated while the details of the procedure are more easily recalled by the provider. Further, as the operative note system 102 provides authentication to allow a provider to sign off on an operative note through a provider device 104, a finalized operative note may be provided to, for example an EMR 106 without waiting for dictation services, printing, scanning in a finalized note, locating a provider, and the like.

Where additional filters and/or parameters are included in the request from the provider device 104, the operative note system 102 may include the parameters when querying the practice management system 108. For example, where the request includes cases with procedures performed on a particular date, the operative note system 102 may query the practice management system 108 for information about cases with surgeries and/or procedures performed on the date included in the request. Where the operative note system 102 queries multiple practice management systems 108, the practice management systems 108 may be associated with different facilities, provider groups, medical groups, and the like. In some examples, the operative note system 102 may obtain additional information related to the cases from one or more EMRs 106. For example, the EMR interface 118 may use EMR data 126 to query an EMR 106 for information regarding the procedure, patient, or other aspect of the cases.

In some examples, the operative note system 102 may identify surgical cases available for operative note generation at regular intervals (e.g., based on user settings). For example, the request from the user device may be a request to identify, at a specific time and interval (e.g., at 9 am each weekday), cases available for operative note generation. In these examples, the operative note system 102 may provide notifications to the provider device 104 and/or other locations (e.g., through sending an e-mail to the provider). Such notifications may include push notifications, text messages, and the like. In some examples, notifications may be provided to the provider device 104 based on an additional condition, such as identification of cases where the procedure took place more than a week (or other interval) before the generation of the notification.

At block 706, the operative note system 102 displays, at the provider device, the surgical cases available for operative note generation at the provider device 104. The cases may be displayed, in some examples, with the user interface 300 or a similar user interface at the provider device 104. To display the cases available for operative note generation, the operative note system 102 may use the information obtained from the practice management system 108 and/or the EMR 106 at block 704. In some examples, the operative note system 102 may determine additional information, such as the status 304*a* of a case based on the information obtained at block 704. The cases may, in some examples, be ordered for display based on the request and/or user settings. For example, the cases may be displayed with the oldest case (e.g., the case where the surgery and/or procedure was performed first) displayed most prominently (e.g., at the top of a list of cases).

The operative note system 102 receives, from the provider device, a request to generate an operative note for one of the surgical cases displayed at the provider device 104 at block 708. The request to generate the operative note may be received, for example, through selection of a recording element 406 at the user interface 400 or at a similar user interface at the provider device 104. In some examples, the request may be received at the user interface generated at block 706 displaying the cases available for operative note generation. For example, the user interface 300 or a similar user interface may include additional elements for requesting generation of an operative note directly from the user interface 300. In some examples, the case elements 302*a* and 302*b* may have selectable elements to request operative note generation. In some examples, a menu may be included in the user interface 300 or a similar user interface 300 allowing the provider to select one or more listed cases for operative note generation.

Figure 9:
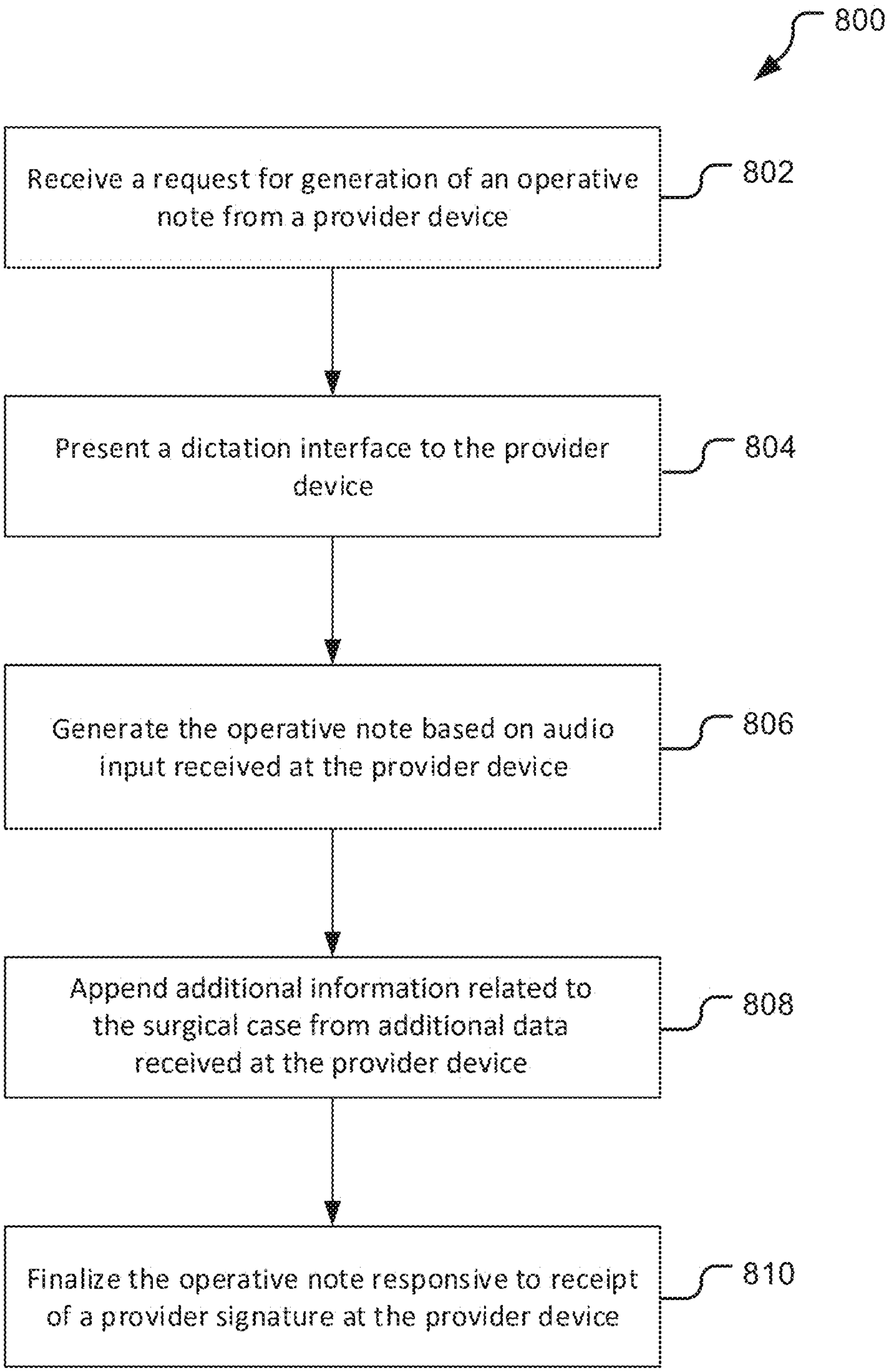
FIG. 9 illustrates example operations for generating an operative note via a dictation interface at a provider device, in accordance with various embodiments of the disclosure.

FIG. 9 illustrates example operations 800 for generating an operative note via a dictation interface at a provider device, in accordance with various embodiments of the disclosure. The operative note system 102 receives a request for generation of an operative note from a provider device 104 at block 802. The request for generation of the operative note may be received, in some examples, as described at block 708 of FIG. 8. In some examples, the request may be generated by another application at the provider device 104. For example, the provider device 104 may include a scheduling application, provider application corresponding to a practice management system 108 and/or an EMR system 106, or other applications which may communicate with an application or web page of the operative note system 102 to generate the request.

At block 804, the operative note system 102 presents a dictation interface to the provider device 104. The dictation interface may be, for example, the dictation interface 500 or a similar interface. In some examples, the dictation interface may be a blank interface, not including template text or other pre-populated fields. To present the dictation interface, dictation interface configuration 120 may access user data 124 or other data to determine whether any dictation templates should be used to generate the dictation interface for the case included in the request. For example, the user data 124 may include a default template specific to the provider and/or a medical group including the provider and associated with the case. Dictation interface configuration 120 may then select the default template where no other templates apply. In some examples, user data 124 may include additional templates and/or rules regarding when templates should be used. For example, the provider associated with the provider device 104 may have templates specific to individual procedures and, when the case is not associated with one of those procedures, instructions to use a default template associated with the provider. Where no templates are specified, dictation interface configuration 120 may present a blank dictation interface.

Some dictation templates may include text to be configured by dictation interface configuration 120 prior to rendering the dictation interface at the provider device 104. Accordingly, dictation interface configuration 120 may obtain additional information and/or choose how to configure such text before providing the dictation interface at the provider device 104. For example, a template may include placeholders for patient name and/or identifier, provider name, procedure date, and/or other information about the patient or procedure. In some examples, the placeholders may include instructions for querying the EMR 106 to obtain the information to be included in the dictation interface. For example, the placeholders or fields may be mapped to a portion or element of the schema of the EMR 106. In these examples, dictation interface configuration 120 may communicate with the EMR interface 118 to obtain the information from the EMR 106. In some examples, the operative note system 102 may further query a practice management system 108 or other medical management system to obtain information for filling a placeholder element and rendering the dictation interface.

At block 806, the operative note system 102 generates the operative note based on audio input received at the provider device 104. To generate the operative note, text generation 122 may receive the audio input from the user device 104 and convert the audio input to text displayed at the dictation interface. In some examples, text generation 122 may convey the audio input to a linked service for text generation. Text generation 122 may include functionality for generating text from audio input at the provider device 104. In some examples, audio input may be collected once a field (e.g., fields 504*b*-504*d* of the dictation interface) of a dictation template is selected. In some examples, the dictation interface may include a recording or microphone element to control when audio input is collected from a microphone of the provider device 104. In some examples, text generation 122 may render text differently responsive to defined keywords (e.g., audio shortcuts) received at the user device 104.

At block 808, the operative note system 102 may append additional information related to the surgical case from additional data received at the provider device 104 and stored on a server, e.g., a cloud computing resource. Such additional data may include text and/or image data. The text and image data may include images captured during the surgery (e.g., photographs, endoscope images, internal ultrasounds, and the like) corresponding to the surgical case and/or data retrieved from other locations related to a surgical implant or other surgical materials used during a surgery or procedure. For example, data related to surgical implants may be obtained by scanning (e.g., taking an image of) a bar code, QR code, or other image identification of an implant used in a surgery or procedure. Such captured data may be used to look up (e.g., in a database at a storage location accessible by the operative note system 102), additional information about the surgical implant, such as serial number, manufacturer, and the like. Such additional information may be stored and/or may be appended to the operative note once captured. In some examples, to append the additional information to the operative note, the operative note system 102 may access the stored data and automatically populate the operative note with the data.

At block 810, the operative note system 102 finalizes an operative note for a surgical case responsive to receipt of a provider signature at a provider device. In some examples, a signature option may be provided in the dictation interface 500 for the provider to sign the operative note. In some examples, a provider may sign off on an operative note using an element (e.g., element 608*c* in the user interface 600) to finalize the operative note and sign off. In some examples, before signing a completed operative note, the operative note system 102 may perform additional verification of the provider device 104 and or the provider associated with the provider device 104. For example, the provider may be prompted to re-enter credentials prior to signing and/or may provide biometric input (e.g., a fingerprint, a facial scan, or the like) to verify that the user of the provider device 104 is the provider and is authorized to sign and finalize the operative note.

In some examples, more than one provider may review and/or sign off on an operative note. In these examples, the operative note system 102 may make a copy of the operative note available to additional providers for signature and/or additions after generation and signature of the operative note by a first provider. For example, a supervising physician may review and/or provide addenda to operative notes prepared by student physicians. In some examples, more information may be added to an operative note by various specialists performing a procedure. In these examples, each provider reviewing the operative note may access the operative note system 102 using a different provider device. After a first provider has finalized or signed off on an operative note, the operative note may be made available for signature at the provider device of another provider signing and/or contributing to the operative note. The operative note system 102 may continue providing copies of the operative note to all providers involved until all the providers have signed the operative note.

Figure 10:
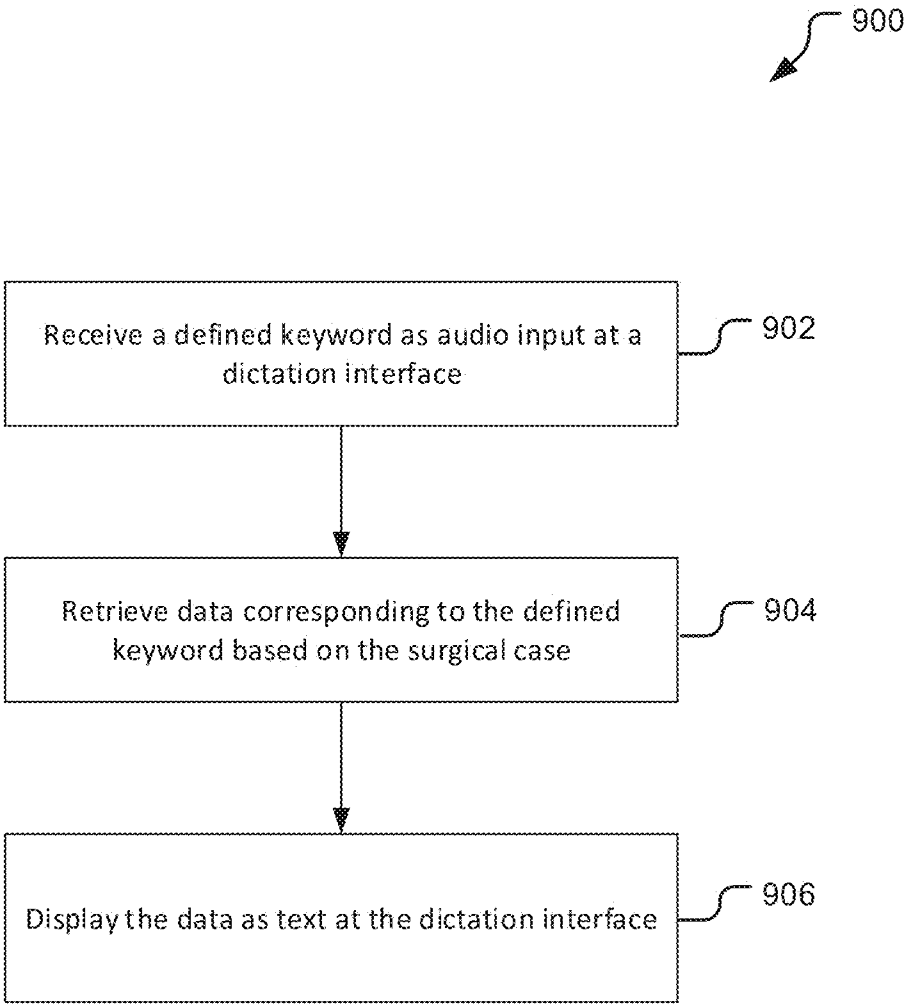
FIG. 10 illustrates example operations for utilizing defined keywords for generation of an operative note, in accordance with various embodiments of the disclosure.

FIG. 10 illustrates example operations 900 for utilizing defined keywords for generation of an operative note, in accordance with various embodiments of the disclosure. In some examples, the operative note system 102 may support defined keywords (also referred to as audio shortcuts) for generating the operative note. For example, a long paragraph or template may be provided responsive to a short spoken phrase at the provider device 104. For example, an audio shortcut may allow the provider to say "normal procedure" (or a similar phrase including a procedure name) to populate the dictation interface with a template reflecting a normal procedure. Similarly, a "normal" audio shortcut may have different meanings depending on the field of a template selected for audio input. For example, where the field 504*b* of the dictation interface 500 is selected, the provider may say "normal" to insert a narration reflecting a normal procedure. Where the field 504*c* is selected, the provider may say "normal" to insert the details of anesthesia routinely used in the procedure. In some examples, audio shortcuts may be used to retrieve specific information about the case from, for example, the EMR 106. For example, saying "patient name" may pull the patient's name from the EMR 106 or from another location. Other information, such as a patient's preoperative diagnosis may be similarly retrieved from the EMR 106 using an audio shortcut. Some audio shortcuts may also be used to automatically insert phrases frequently used by the provider.

At block 902, the operative note system 102 receives a defined keyword as audio input at a dictation interface. For example, text generation 122 may determine whether audio input corresponds to a defined audio shortcut by referencing, for example, audio shortcuts defined in the user data 124 as audio input is received. An audio shortcut or defined keyword may be specific to a provider, group of providers, facility, surgical specialty, or other grouping of users. Accordingly, text generation 122 may reference audio shortcuts applicable to the case and operative note being generated when determining whether audio input corresponds to a defined keyword.

The operative note system 102 retrieves data corresponding to the defined keyword based on the surgical case at block 904. Text generation 122 may, depending on the type of audio shortcut, insert text and/or coordinate with other elements of the operative note system 102 (e.g., EMR interface 118) to obtain information corresponding to the audio shortcut. For example, text generation 122 may insert text saved with user data 124 reflecting a normal procedure in response to a "normal" audio shortcut. In response to an audio shortcut mapped to a field of the EMR 106, text generation 122 may coordinate with the EMR interface 118 to obtain the information and render the text at the dictation interface 500.

At block 906, the operative note system 102 displays the data as text at the dictation interface. After the data is retrieved by text generation 122, dictation interface configuration 120 provides text corresponding to the data at the dictation interface 500. In some examples, after providing the text at the dictation interface, the dictation interface 500 may continue receiving audio input as normal. For example, after a patient name is inserted, a cursor or other placeholder may remain in the same field and the provider may continue dictating to the provider device 104 without re-selecting a field, turning on audio dictation, and the like. In some examples, the text may be rendered and the user may select a field, turn on dictation, or perform other actions to continue dictation. For example, some audio shortcuts may be used to provide a template not provided when rendering the dictation interface. Accordingly, the provider may select a field of the newly provided dictation template to continue with dictation.

Figure 11:
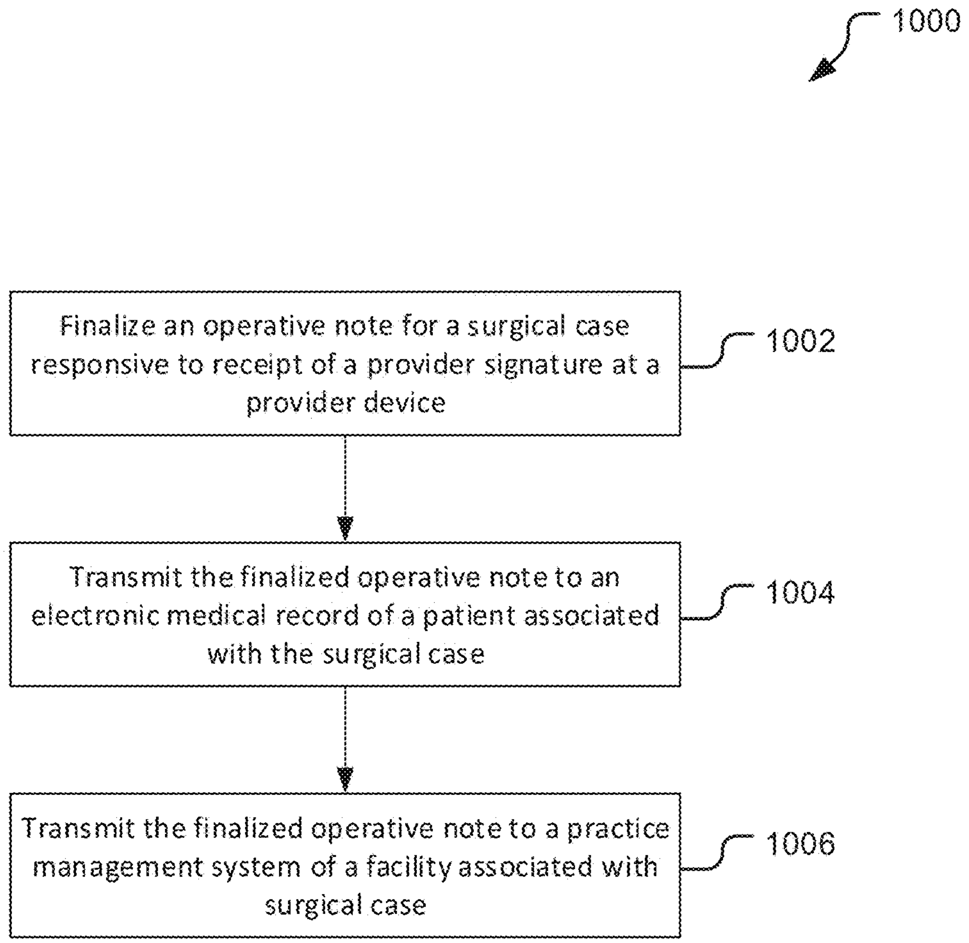
FIG. 11 illustrates example operations for finalizing an operative note generated using a provider device, in accordance with various embodiments of the disclosure.

FIG. 11 illustrates example operations 1000 for finalizing an operative note generated using a provider device 104, in accordance with various embodiments of the disclosure. At block 1002, the operative note system 102 finalizes an operative note for a surgical case responsive to receipt of a provider signature at a provider device. In some examples, a signature option may be provided in the dictation interface 500 for the provider to sign the operative note. In some examples, a provider may sign off on an operative note using an element (e.g., element 608*c* in the user interface 600) to finalize the operative note and sign off. In some examples, before signing a completed operative note, the operative note system 102 may perform additional verification of the provider device 104 and or the provider associated with the provider device 104. For example, the provider may be prompted to re-enter credentials prior to signing and/or may provide biometric input (e.g., a fingerprint, a facial scan, or the like) to verify that the user of the provider device 104 is the provider and is authorized to sign and finalize the operative note.

In some examples, more than one provider may review and/or sign off on an operative note. In these examples, the operative note system 102 may make a copy of the operative note available to additional providers for signature and/or additions after generation and signature of the operative note by a first provider. For example, a supervising physician may review and/or provide addenda to operative notes prepared by student physicians. In some examples, more information may be added to an operative note by various specialists performing a procedure. In these examples, each provider reviewing the operative note may access the operative note system 102 using a different provider device. After a first provider has finalized or signed off on an operative note, the operative note may be made available for signature at the provider device of another provider signing and/or contributing to the operative note. The operative note system 102 may continue providing copies of the operative note to all providers involved until all the providers have signed the operative note.

The operative note system 102 transmits the finalized operative note to an electronic medical record of a patient associated with the surgical case at block 1004. The EMR interface 118 may transmit the finalized operative note directly to the EMR 106 once the operative note is signed and finalized by the provider. To transmit the finalized operative note, the EMR interface 118 may use the EMR data 126 to determine parameters, headers, or other information to send with the operative note to the EMR 106 to ensure the operative note is placed in the appropriate patient record. The EMR interface 118 may, in some examples, receive additional input from the provider device 104 before sending the operative note to the EMR 106.

Similarly, the operative note system 102 transmits the finalized operative note to a practice management system of a facility associated with the surgical case at block 1006. Transmission of the finalized operative note may be automatic (e.g., triggered by signing of the operative note at the provider device 104) or may be performed responsive to additional input at the provider device 104 (e.g., the provider selecting an option to send the operative note to the practice management system 108.

Once the operative note has been transmitted to an EMR 106 or 107, the operative note may be viewed by users with access to the EMR, including, for example, other providers and the patient (e.g., through a patient portal). As the operative note system 102 allows for immediate generation of operative notes, accurate information about a procedure may be available to a patient and other providers treating the patient shortly after completion of a procedure or surgery. Once the operative note is transmitted to a practice management system 108 or 109, a surgery center or other facility may be able to view the operative note and complete other activities relating to the procedure, such as billing for the procedure or surgery.

The systems and methods described above allow a provider device 104 to interface with EMRs 106 and 107, practice management systems 108 and 109, and other systems to streamline the process of dictation and generation of operative notes by allowing a provider device 104 to serve as an interface for dictation and an secure device for signing and transmitting medical information. Accordingly, providers are able to quickly generate operative notes, increasing accuracy and improving on manual processes for operative note generation. The operative note system 102 provides access to the EMR 106, allowing providers to access information from the EMR 106 and to transmit operative notes to the EMR 106 more promptly following a surgery or procedure. The operative note system 102 further provides access to practice management systems 108, allowing surgical facilities to more easily track and receive operative notes for procedures performed at the facilities. By providing access to multiple EMRs 106 and 107 and multiple practice management systems 108 and 109, the practice management system 102 further allows the provider to use one interface to generate operative notes for procedures performed at, for example, different surgical centers, further simplifying the provider's workflow and the process of updating medical records. By providing authentication to each of the connected systems, the operative note system 102 further allows for secure transmission of medical information to and from a provider device.

The technology described herein may be implemented as logical operations and/or modules in one or more systems.

The logical operations may be implemented as a sequence of processor-implemented steps directed by software programs executing in one or more computer systems and as interconnected machine or circuit modules within one or more computer systems, or as a combination of both. Likewise, the descriptions of various component modules may be provided in terms of operations executed or effected by the modules. The resulting implementation is a matter of choice, dependent on the performance requirements of the underlying system implementing the described technology. Accordingly, the logical operations making up the embodiments of the technology described herein are referred to variously as operations, steps, objects, or modules. Furthermore, it should be understood that logical operations may be performed in any order, unless explicitly claimed otherwise or a specific order is inherently necessitated by the claim language.

In some implementations, articles of manufacture are provided as computer program products that cause the instantiation of operations on a computer system to implement the procedural operations. One implementation of a computer program product provides a non-transitory computer program storage medium readable by a computer system and encoding a computer program. It should further be understood that the described technology may be employed in special purpose devices independent of a personal computer.

The above specification, examples and data provide a complete description of the structure and use of exemplary embodiments of the invention as defined in the claims. Although various embodiments of the claimed invention have been described above with a certain degree of particularity, or with reference to one or more individual embodiments, it is appreciated that numerous alterations to the disclosed embodiments without departing from the spirit or scope of the claimed invention may be possible. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

The invention claimed is:

1. A method for generating operative notes for medical procedures, the method comprising:

providing, to a first practice management system of a first facility associated with medical procedures, a first query for a first list of one or more cases that are each associated with an operative note to be completed, the first query comprising a first application programming interface (API) and first fields of the first practice management system;

providing, to a second practice management system of a second facility associated with medical procedures, a second query for a second list of one or more cases that are each associated with an operative note to be completed, the second query comprising a second API and second fields of the second practice management system, wherein the second API differs from the first API, the second facility differs from the first facility, the second practice management system differs from the first practice management system, the second list differs from the first list, and the first API, the first fields, the second API, and the second fields are based on stored electronic medical record data;

receiving, from the first practice management system responsive to the first query, the first list of one or more cases that are each associated with an operative note to be completed;

receiving, from the second practice management system responsive to the second query, the second list of one or more cases that are each associated with an operative note to be completed;

transmitting, to a provider device, a user interface configured to present selectable elements, the selectable elements comprising the first list of one or more cases and the second list of one or more cases;

in response to receiving a selection of an element associated with a case in either the first list of one or more cases or the second list of one or more cases, transmitting a dictation interface to the provider device, the dictation interface configured to present information associated with the case and a selectable recording element;

responsive to receipt of a selection of the recording element, receiving audio input associated with the case from the provider device;

transmitting, to the provider device, the operative note by displaying, in the dictation interface, text generated based on the audio input;

finalizing the operative note responsive to receipt of a selection of a selectable element indicating provider approval of the operative note, wherein the provider approval is authorized based on an electronic medical record associated with a patient identifier;

transmitting the finalized operative note to the electronic medical record; and transmitting the finalized operative note to either the first practice management system of the first facility or the second practice management system of the second facility based on the case being associated with the first facility or the second facility.

2. The method of claim 1, wherein transmitting the operative note further comprises adding, to the operative note, one or more images captured by a device during an appointment for a medical procedure, wherein the one or more images are received from a cloud computing device.

3. The method of claim 1, wherein transmitting the operative note further comprises adding, to the operative note, information related to an image captured by a device during an appointment for a medical procedure, wherein:

the image is of an identifier related to a medical material used during the appointment and the information is related to the medical material; and the image is received from a cloud computing device.

4. The method of claim 3, wherein the medical material comprises an implant.

5. The method of claim 1, further comprising generating the dictation interface by identifying a plurality of dictation fields for inclusion in the dictation interface, wherein the plurality of dictation fields is identified based on a medical procedure associated with an appointment.

6. The method of claim 5, wherein generating the dictation interface further comprises selecting default text for one or more of the identified dictation fields of the operative note based on the medical procedure associated with the appointment, wherein the dictation interface includes the default text and the plurality of dictation fields.

7. A system to generate operative notes for medical procedures, the system comprising:

one or more processors; and memory encoding:

data fields of a plurality of practice management systems as electronic medical record (EMR) data; and instructions which, when executed by the one or more processors, cause the system to perform operations comprising:

providing, to a first practice management system of a first medical facility in communication with the system, a first query for a first list of one or more cases that are each associated with an operative note to be completed, the first query comprising a first application programming interface (API) and one or more data fields that are associated with EMR data of the first practice management system;

providing, to a second practice management system of a second medical facility in communication with the system, a second query for a second list of one or more cases that are each associated with an operative note to be completed, the second query comprising a second API and one or more data fields that are associated with EMR data of the second practice management system, wherein the second API differs from the first API, the second facility differs from the first facility, the second practice management system differs from the first practice management system, and the second list differs from the first list;

receiving, responsive to the first query, the first list of one or more cases that are each associated with an operative note to be completed;

receiving, responsive to the second query, the second list of one or more cases that are each associated with an operative note to be completed;

transmitting, to a provider device in communication with the system, a user interface configured to present the first list of one or more cases and the second list of one or more cases;

in response to receiving a selection of a case in either the first list of one or more cases or the second list of one or more cases, transmitting a dictation interface to the provider device, the dictation interface configured to present a recording element and one or more elements that are rendered based on information received by the system from an electronic medical record using a patient identifier;

responsive to receipt of a selection of the recording element, receiving audio input associated with the case from the provider device;

generating the operative note by displaying, in the dictation interface, text generated based on the audio input;

transmitting the generated operative note to the electronic medical record associated with the patient identifier; and transmitting the generated operative note to either the first practice management system of the first facility or the second practice management system of the second facility based on the case being associated with the first facility or the second facility.

8. The system of claim 7, wherein the memory encoding instructions further cause the system to perform operations comprising at least one of:

adding one or more images of a patient to the operative note, the one or more images of the patient captured during a medical procedure; or adding information to the operative note, the information related to one of an implant or surgical materials used during the medical procedure.

9. The system of claim 7, wherein:

the dictation interface is further rendered to display a dictation template; and the memory encoding instructions further cause the system to perform operations comprising identifying the dictation template from a plurality of dictation templates based on data associated with an appointment for a medical procedure.

10. The system of claim 9, wherein the dictation template is rendered responsive to a dictation command received as audio input from the provider device.

11. The system of claim 9, wherein:

the dictation interface includes at least one selectable field; and the memory encoding instructions further cause the system to perform operations comprising selecting text to fill the at least one selectable field from the electronic medical record.

12. The system of claim 9, wherein the dictation template is specific to the appointment for the medical procedure.

13. The system of claim 9, wherein the memory encoding instructions further cause the system to perform operations comprising:

analyzing the data associated with the appointment to retrieve one or more of standard vocabulary, stock language, default descriptions, or defined texts related to the medical procedure associated with the appointment; and populating the dictation template with the one or more of standard vocabulary, stock language, default descriptions, or defined texts.

14. The system of claim 7, wherein transmitting the operative note further comprises authenticating a signature received by the system using one or more of a credential of the provider device or a credential of a provider received from the provider device.

15. The system of claim 7, wherein displaying, in the dictation interface, text generated based on the audio input received from the provider device includes selecting text based on a defined dictation shortcut received as audio input from the provider device.

16. One or more non-transitory computer readable media encoded with instructions to generate operative notes for medical procedures that, when executed by one or more processors of an operative note system, cause the operative note system to perform operations comprising:

receiving, from a provider device, a first request to view a first listing of cases associated with a provider, the first request comprising one or more first criteria to filter cases associated with the provider, the one or more first criteria comprising a period of time, a type of medical procedure, or a first medical facility, the first request comprising one or more data fields of a first practice management system associated with the provider;

receiving, from a provider device, a second request to view a second listing of cases associated with the provider, the second request comprising one or more second criteria to filter cases associated with the provider, the one or more second criteria comprising the period of time, the type of medical procedure, or a second medical facility, wherein the second request comprises one or more data fields of a second practice management system associated with the provider, and the second request differs from the first request, the second listing differs from the first listing, the second medical facility differs from the first medical facility, and the second practice management system differs from the first practice management system;

responsive to the first request, receiving, from the first practice management system, a first list of one or more cases that are associated with the one or more first criteria;

responsive to the second request, receiving, from the second practice management system, a second list of one or more cases that are associated with the one or more second criteria;

transmitting, to a provider device, a user interface configured to present the first list of one or more cases and the second list of one or more cases;

responsive to receiving a selection of a case in either the first list of one or more cases of the second list of one or more cases, transmitting a dictation interface to the provider device, the dictation interface presenting a plurality of selectable text fields and a recording element;

receiving a selection of a text field in the plurality of selectable text fields;

receiving audio input in response to a selection of the recording element;

generating the operative note by providing text in the selected field, the text generated based on the audio input;

transmitting the operative note to the provider device;

finalizing the operative note responsive to receipt of a provider approval indicating accuracy and approval of the operative note;

transmitting the finalized operative note to an electronic medical record associated with a patient identifier; and transmitting the finalized operative note to either the first practice management system of the first facility or the second practice management system of the second facility based on the cases being associated with the first facility or the second facility.

17. The one or more non-transitory computer readable media of claim 16, wherein:

the operations further comprise generating the dictation interface by identifying the plurality of selectable text fields for inclusion in the dictation interface;

the plurality of selectable text fields are identified based on a medical procedure; and the plurality of selectable text fields are mapped to a plurality fields of the electronic medical record associated with the patient identifier.

18. The one or more non-transitory computer readable media of claim 16, wherein the operations further comprise:

transmitting the finalized operative note to a practice management system of a facility associated with the provider, wherein the transmitted operative note includes information correlating the operative note to an appointment with the medical provider using data about the practice management system.

19. The one or more non-transitory computer readable media of claim 16, wherein generating the operative note further comprises receiving, from the electronic medical record, patient data responsive to receipt, through the dictation interface, of audio data corresponding to a keyword associated with the patient data.

20. The one or more non-transitory computer readable media of claim 16, wherein the operations further comprise:

generating the dictation interface by selecting a dictation template including default text and the plurality of selectable text fields, wherein the dictation template is selected based on a dictation keyword received as audio input from the provider device.

* * * * *